United States Patent
Zou et al.

(10) Patent No.: US 8,715,937 B2
(45) Date of Patent: *May 6, 2014

(54) MUTATION DETECTION ASSAY

(75) Inventors: Hongzhi Zou, Middleton, WI (US); Graham P. Lidgard, Madison, WI (US); Michael J. Domanico, Middleton, WI (US); Hatim Allawi, Middleton, WI (US)

(73) Assignee: Exact Sciences Corporation, Madison, WI (US)

( * ) Notice: Subject to any disclaimer, the term of this patent is extended or adjusted under 35 U.S.C. 154(b) by 598 days.

This patent is subject to a terminal disclaimer.

(21) Appl. No.: 12/946,752

(22) Filed: Nov. 15, 2010

(65) Prior Publication Data
US 2012/0122106 A1 May 17, 2012

(51) Int. Cl.
*C12Q 1/68* (2006.01)
*C12P 19/34* (2006.01)

(52) U.S. Cl.
USPC .......................................... 435/6.12; 435/91.2

(58) Field of Classification Search
None
See application file for complete search history.

(56) References Cited

U.S. PATENT DOCUMENTS

| | | | |
|---|---|---|---|
| 5,541,311 A | 7/1996 | Dahlberg et al. | |
| 5,614,402 A | 3/1997 | Dahlberg et al. | |
| 5,624,819 A * | 4/1997 | Skolnick et al. | 435/69.1 |
| 5,719,028 A | 2/1998 | Dahlberg et al. | |
| 5,795,763 A | 8/1998 | Dahlberg et al. | |
| 5,837,450 A | 11/1998 | Dahlberg et al. | |
| 5,843,654 A | 12/1998 | Heisler et al. | |
| 5,843,669 A | 12/1998 | Kaiser et al. | |
| 5,846,717 A | 12/1998 | Brow et al. | |
| 5,874,283 A | 2/1999 | Harrington et al. | |
| 5,888,780 A | 3/1999 | Dahlberg et al. | |
| 5,985,557 A | 11/1999 | Prudent et al. | |
| 5,994,069 A | 11/1999 | Hall et al. | |
| 6,001,567 A | 12/1999 | Brow et al. | |
| 6,090,543 A | 7/2000 | Prudent et al. | |
| 6,090,606 A | 7/2000 | Kaiser et al. | |
| 6,194,149 B1 | 2/2001 | Neri et al. | |
| 6,210,880 B1 | 4/2001 | Lyamichev et al. | |
| 6,214,545 B1 | 4/2001 | Dong et al. | |
| 6,348,314 B1 | 2/2002 | Prudent et al. | |
| 6,355,437 B1 | 3/2002 | Neri et al. | |

(Continued)

OTHER PUBLICATIONS

Hosono et al. (Hum Mutat. Jan. 2008;29(1):182-9).*

(Continued)

*Primary Examiner* — Kenneth Horlick
(74) *Attorney, Agent, or Firm* — James S. Keddie; Bozicevic, Field & Francis, LLP

(57) ABSTRACT

A method of sample analysis is provided. In certain embodiments, the method involves: a) amplifying a product from a sample that comprises both wild type copies of a genomic locus and mutant copies of the genomic locus that have a point mutation relative to the wild type copies of the genomic locus, to produce an amplified sample, where: i. the amplifying is done using a first primer and a second primer; and ii. the first primer comprises a 3' terminal nucleotide that base pairs with the point mutation and also comprises a nucleotide sequence that is fully complementary to a sequence in the locus with the exception of a single base mismatch within 6 bases of the 3' terminal nucleotide; and b) detecting the presence of the product in the amplified sample using a flap assay that employs an invasive oligonucleotide. A kit for performing the method is also provided.

17 Claims, 13 Drawing Sheets

(56) References Cited

U.S. PATENT DOCUMENTS

| | | |
|---|---|---|
| 6,358,691 B1 | 3/2002 | Neri et al. |
| 6,372,424 B1 | 4/2002 | Brow et al. |
| 6,458,535 B1 | 10/2002 | Hall et al. |
| 6,555,357 B1 | 4/2003 | Kaiser et al. |
| 6,562,611 B1 | 5/2003 | Kaiser et al. |
| 6,635,463 B2 | 10/2003 | Ma et al. |
| 6,673,616 B1 | 1/2004 | Dahlberg et al. |
| 6,692,917 B2 | 2/2004 | Neri et al. |
| 6,706,471 B1 | 3/2004 | Brow et al. |
| 6,709,815 B1 | 3/2004 | Dong et al. |
| 6,709,819 B2 | 3/2004 | Lyamichev et al. |
| 6,759,226 B1 | 7/2004 | Ma et al. |
| 6,780,585 B1 | 8/2004 | Dong et al. |
| 6,780,982 B2 | 8/2004 | Lyamichev et al. |
| 6,872,816 B1 | 3/2005 | Hall et al. |
| 6,875,572 B2 | 4/2005 | Prudent et al. |
| 6,913,881 B1 | 7/2005 | Aizenstein et al. |
| 6,932,943 B1 | 8/2005 | Cracauer et al. |
| 7,011,944 B2 | 3/2006 | Prudent et al. |
| 7,045,289 B2 | 5/2006 | Allawi et al. |
| 7,060,436 B2 | 6/2006 | Lyamichev et al. |
| 7,067,643 B2 | 6/2006 | Dahlberg et al. |
| 7,087,381 B2 | 8/2006 | Dahlberg et al. |
| 7,101,672 B2 | 9/2006 | Dong et al. |
| 7,122,364 B1 | 10/2006 | Lyamichev et al. |
| 7,150,982 B2 | 12/2006 | Allawi et al. |
| 7,195,871 B2 | 3/2007 | Lyamichev et al. |
| 7,256,020 B2 | 8/2007 | Lyamichev et al. |
| 7,273,696 B2 | 9/2007 | Dahlberg et al. |
| 7,297,780 B2 | 11/2007 | Skrzypczynski et al. |
| 7,306,917 B2 | 12/2007 | Prudent et al. |
| 7,312,033 B2 | 12/2007 | Accola et al. |
| 7,354,708 B2 | 4/2008 | Hall et al. |
| 7,381,530 B2 | 6/2008 | Hall et al. |
| 7,384,746 B2 | 6/2008 | Lyamichev et al. |
| 7,407,782 B2 | 8/2008 | Prudent et al. |
| 7,429,455 B2 | 9/2008 | Dong et al. |
| 7,432,048 B2 | 10/2008 | Neri et al. |
| 7,435,390 B2 | 10/2008 | Cracauer et al. |
| 7,462,451 B2 | 12/2008 | Skrzypczynski et al. |
| 7,473,773 B2 | 1/2009 | Elagin et al. |
| 7,482,118 B2 | 1/2009 | Allawi et al. |
| 7,482,127 B2 | 1/2009 | Agarwal et al. |
| 7,514,220 B2 | 4/2009 | Hall et al. |
| 7,527,928 B2 | 5/2009 | Neri et al. |
| 7,527,948 B2 | 5/2009 | Hudson et al. |
| 7,541,145 B2 | 6/2009 | Prudent et al. |
| 7,582,436 B2 | 9/2009 | Hall et al. |
| 7,588,891 B2 | 9/2009 | Prudent et al. |
| 7,601,496 B2 | 10/2009 | Dahlberg et al. |
| 7,674,924 B2 | 3/2010 | Skrzypczynski et al. |
| 7,678,542 B2 | 3/2010 | Lyamichev et al. |
| 7,691,573 B2 | 4/2010 | Dahlberg et al. |
| 7,700,750 B2 | 4/2010 | Mast et al. |
| 2002/0128465 A1 | 9/2002 | Lyamichev et al. |
| 2002/0142454 A1 | 10/2002 | Cracauer et al. |
| 2002/0156255 A1 | 10/2002 | Cracauer et al. |
| 2002/0198693 A1 | 12/2002 | Marusich et al. |
| 2003/0072689 A1 | 4/2003 | Cracauer et al. |
| 2003/0082544 A1 | 5/2003 | Fors et al. |
| 2003/0092039 A1 | 5/2003 | Olson-Munoz et al. |
| 2003/0104378 A1 | 6/2003 | Allawi et al. |
| 2003/0104470 A1 | 6/2003 | Fors et al. |
| 2003/0113236 A1 | 6/2003 | Cracauer et al. |
| 2003/0113237 A1 | 6/2003 | Cracauer et al. |
| 2003/0124526 A1 | 7/2003 | Cracauer et al. |
| 2003/0134349 A1 | 7/2003 | Ma et al. |
| 2003/0143535 A1 | 7/2003 | Lyamichev et al. |
| 2003/0165954 A1 | 9/2003 | Katagiri et al. |
| 2003/0186238 A1 | 10/2003 | Allawi et al. |
| 2003/0219784 A1 | 11/2003 | Ip et al. |
| 2004/0014067 A1 | 1/2004 | Lyamichev et al. |
| 2004/0018489 A1 | 1/2004 | Ma et al. |
| 2004/0096874 A1 | 5/2004 | Neville et al. |
| 2004/0203035 A1 | 10/2004 | Mast et al. |
| 2004/0219576 A1 | 11/2004 | Skrzypczynski et al. |
| 2004/0235024 A1 | 11/2004 | Lyamichev et al. |
| 2005/0048527 A1 | 3/2005 | Allawi et al. |
| 2005/0074788 A1 | 4/2005 | Dahlberg et al. |
| 2005/0106596 A1 | 5/2005 | Skrzypczynski et al. |
| 2005/0130179 A1 | 6/2005 | Lyamichev et al. |
| 2005/0158716 A1 | 7/2005 | Dahlberg et al. |
| 2005/0164177 A1 | 7/2005 | Neri et al. |
| 2005/0181435 A1 | 8/2005 | Prudent et al. |
| 2005/0186588 A1 | 8/2005 | Lyamichev et al. |
| 2005/0196750 A1 | 9/2005 | Elagin et al. |
| 2005/0277138 A1 | 12/2005 | Skrzypczynski et al. |
| 2006/0147938 A1 | 7/2006 | Accola et al. |
| 2006/0147955 A1 | 7/2006 | Allawi et al. |
| 2006/0160074 A1 | 7/2006 | Dorn et al. |
| 2006/0183207 A1 | 8/2006 | Lyamichev et al. |
| 2006/0198709 A1 | 9/2006 | Marusich et al. |
| 2006/0199202 A1 | 9/2006 | Lyamichev et al. |
| 2006/0234252 A1 | 10/2006 | Andersen |
| 2006/0240452 A1 | 10/2006 | Skrzypczynski et al. |
| 2006/0246475 A1 | 11/2006 | Peterson et al. |
| 2006/0252032 A1 | 11/2006 | Aslanukov et al. |
| 2007/0049745 A1 | 3/2007 | Skrzypczynski et al. |
| 2007/0087345 A1 | 4/2007 | Olson-Munoz et al. |
| 2007/0111200 A1 | 5/2007 | Hudson et al. |
| 2007/0134249 A1 | 6/2007 | Denney et al. |
| 2007/0202517 A1 | 8/2007 | Agarwal et al. |
| 2007/0207455 A1 | 9/2007 | Law et al. |
| 2007/0292856 A1 | 12/2007 | Lyamichev et al. |
| 2008/0014124 A1 | 1/2008 | Skrzypczynski et al. |
| 2008/0015349 A1 | 1/2008 | Skrzypczynski et al. |
| 2008/0032305 A1 | 2/2008 | Dorn et al. |
| 2008/0071074 A1 | 3/2008 | Skrzypczynski et al. |
| 2008/0131870 A1 | 6/2008 | Allawi et al. |
| 2008/0131875 A1 | 6/2008 | Hall et al. |
| 2008/0131890 A1 | 6/2008 | Allawi et al. |
| 2008/0145852 A1* | 6/2008 | Shuber .............................. 435/6 |
| 2008/0160524 A1 | 7/2008 | Ma et al. |
| 2008/0176215 A1 | 7/2008 | Hudson et al. |
| 2008/0181823 A1 | 7/2008 | Iszczyszyn et al. |
| 2008/0182254 A1 | 7/2008 | Hall et al. |
| 2008/0182980 A1 | 7/2008 | Skrzypczynski et al. |
| 2008/0187919 A1 | 8/2008 | King et al. |
| 2008/0187926 A1 | 8/2008 | Dahlberg et al. |
| 2008/0188375 A1 | 8/2008 | Neri et al. |
| 2008/0199936 A1 | 8/2008 | Lyamichev et al. |
| 2008/0213767 A1 | 9/2008 | Western et al. |
| 2008/0220425 A1 | 9/2008 | Ma et al. |
| 2008/0261220 A1 | 10/2008 | Cracauer et al. |
| 2008/0268455 A1 | 10/2008 | Hall et al. |
| 2008/0293046 A1 | 11/2008 | Allawi et al. |
| 2009/0029869 A1 | 1/2009 | Skrzypczynski et al. |
| 2009/0041634 A1 | 2/2009 | Cracauer et al. |
| 2009/0068664 A1 | 3/2009 | Lyamichev et al. |
| 2009/0075256 A1 | 3/2009 | Lyamichev et al. |
| 2009/0078574 A1 | 3/2009 | Lyamichev et al. |
| 2009/0111092 A1 | 4/2009 | Elagin et al. |
| 2009/0117576 A1 | 5/2009 | Dong et al. |
| 2009/0142752 A1 | 6/2009 | Hall et al. |
| 2009/0142754 A1 | 6/2009 | Allawi et al. |
| 2009/0203018 A1 | 8/2009 | Agarwal et al. |
| 2009/0215043 A1 | 8/2009 | Kwitek et al. |
| 2009/0253142 A1* | 10/2009 | Allawi et al. .................... 435/6 |
| 2009/0299641 A1 | 12/2009 | Allawi et al. |
| 2009/0305283 A1 | 12/2009 | Prudent et al. |
| 2010/0152431 A1 | 6/2010 | Skrzypczynski et al. |

OTHER PUBLICATIONS

Okimoto et al. (Biotechniques. Jul. 1996;21(1):20-2, 24, 26).*

Allawi, et al., "Invader plus method detects herpes simplex virus in cerebrospinal fluid and simultaneously differentiates types 1 and 2", J Clin Microbiol., 2006, 44:3443-7.

Applied Biosystems, "Methylation Analysis by Bisulfite Sequencing: Chemistry, Products and Protocols from Applied Biosystems", 2007, 52pgs.

Eads, et al., "MethyLight: a high-throughput assay to measure DNA methylation", Nucleic Acids Res., 2000, 28:E32, 8pgs.

(56) References Cited

OTHER PUBLICATIONS

Herman, et al., "Methylation-specific PCR: a novel PCR assay for methylation status of CpG islands", Proc Natl Acad Sci., 1996, 93:9821-6.

Itzkowitz, et al., "A simplified, noninvasive stool DNA test for colorectal cancer detection", Am J Gastroenterol., 2008, 103:2862-70.

Itzkowitz, et al., "Improved fecal DNA test for colorectal cancer screening", Clin Gastroenterol Hepatol., 2007, 5:111-7.

Qiagen, "EpiTect® MethyLight PCR Handbook", MethyLight PCR Kit, MethyLight PCR + ROX Vial Kit, 2008, 36pgs.

Tadokoro, et al., "Quantitation of viral load by real-time PCR-monitoring Invader reaction", J Virol Methods., 2009, 155:182-6.

Yamada, et al., "Fluorometric identification of 5-methylcytosine modification in DNA: combination of photosensitized oxidation and invasive cleavage", Bioconjug Chem., 2008, 19:20-3.

Zymo Research Corp., "EZ DNA Methylation-Gold™ Kit", Flyer, Catalog Nos. D5005 & D5006, Ver. 2.1.0 downloaded Feb. 23, 2011, 2pgs.

Zymo Research Corp., "EZ DNA Methylation-Gold™ Kit", Instructions, Catalog Nos. D5005 & D5006, Ver. 2.1.0, downloaded Feb. 23, 2011, 10pgs.

Zymo Research Corp., "EZ DNA Methylation™ Kit", Instruction Manual, Catalog Nos. D5001 & D5002, Ver. 1.2.2, downloaded Feb. 23, 2011, 10pgs.

Zymo Research Corp., "Material Safety Data Sheet", MSDS: CT Conversion Reagent, Creation Date: Apr. 28, 2003, Revision Date: May 4, 2009, 1-4.

PCT/US11/58993, International Search Report and Written Opinion, mailed Feb. 17, 2012, 12pgs.

Kaiser, et al., A comparison of eubacterial and archaeal structure-specific 5'-Exonucleases, J Biol Chem, 1999, 274:21387-94.

* cited by examiner

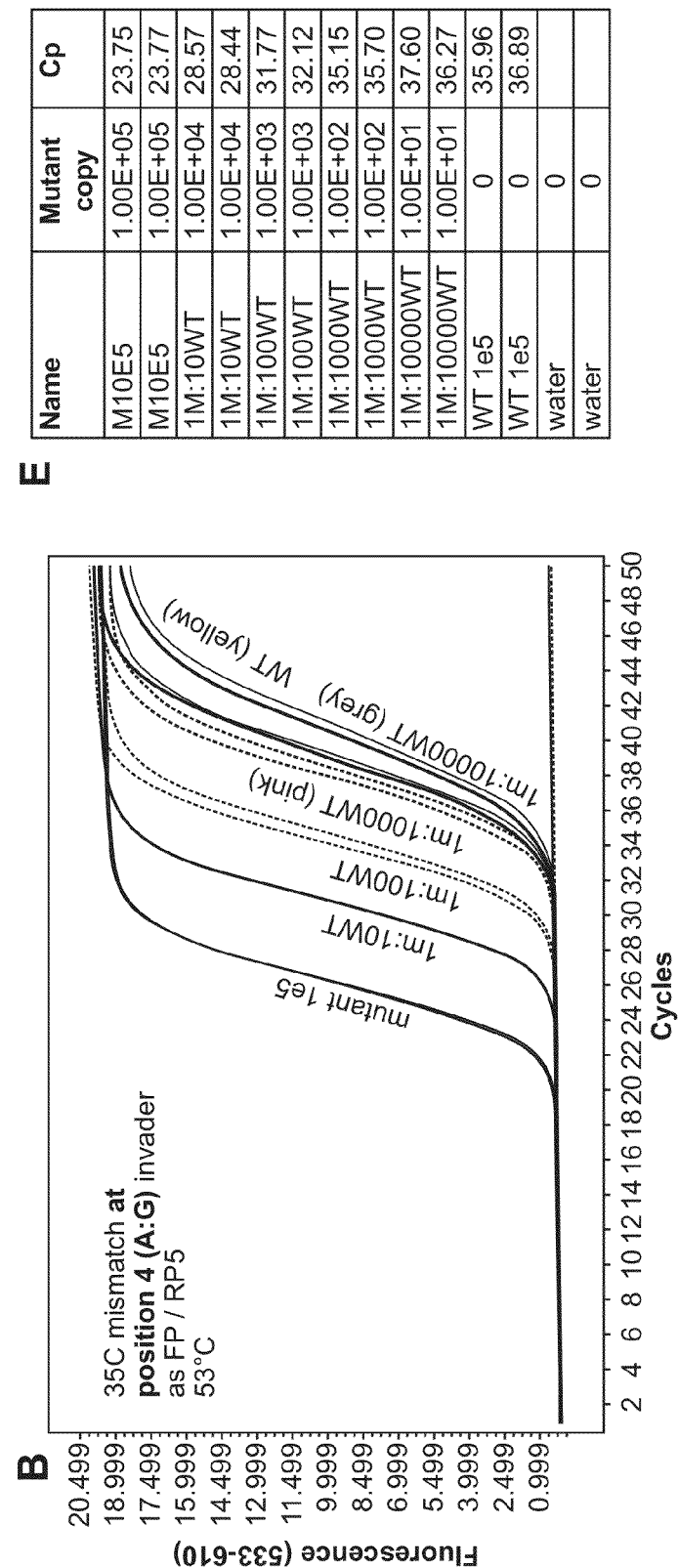
FIG. 5 (Cont. 1)

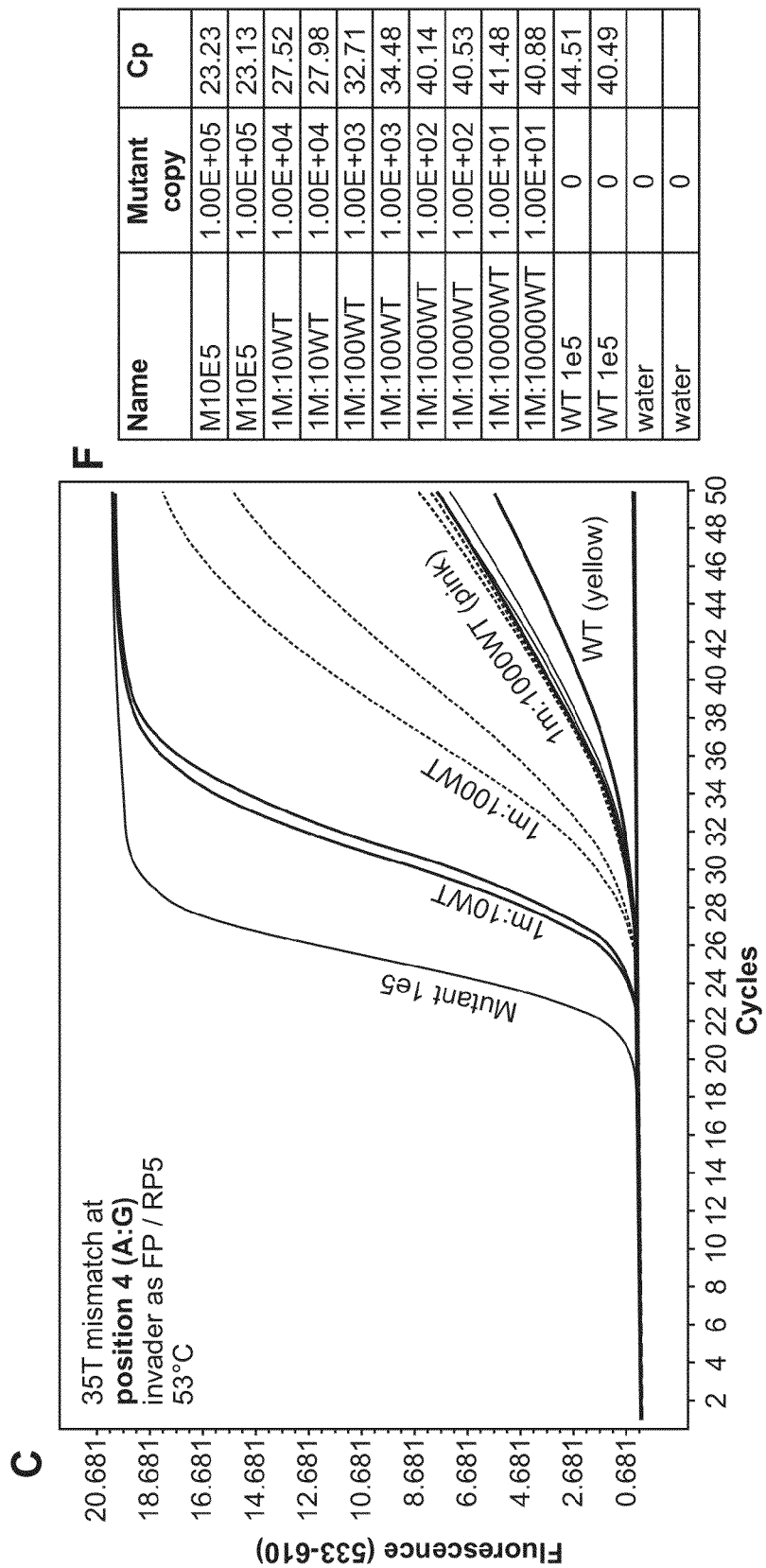
FIG. 5 (Cont. 2)

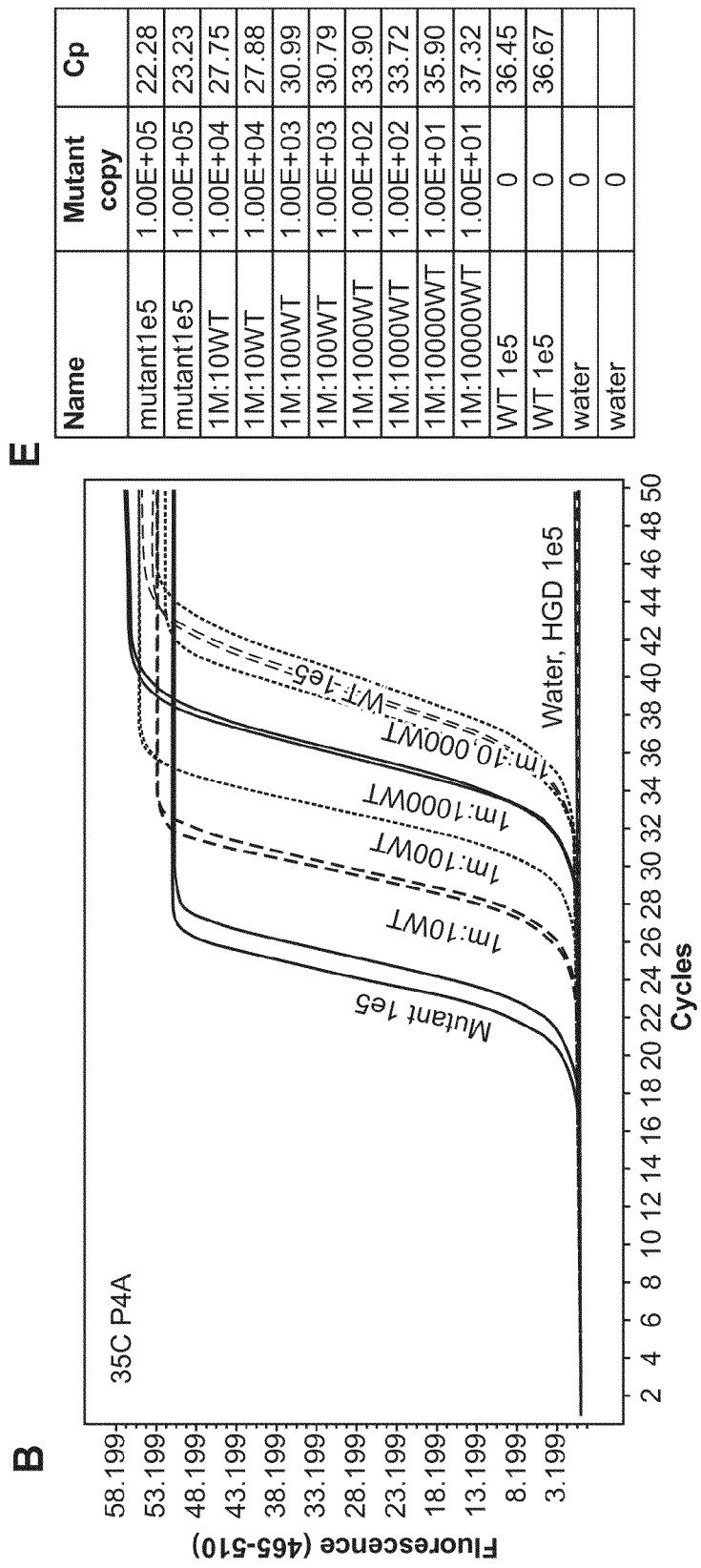
FIG. 6 (Cont. 1)

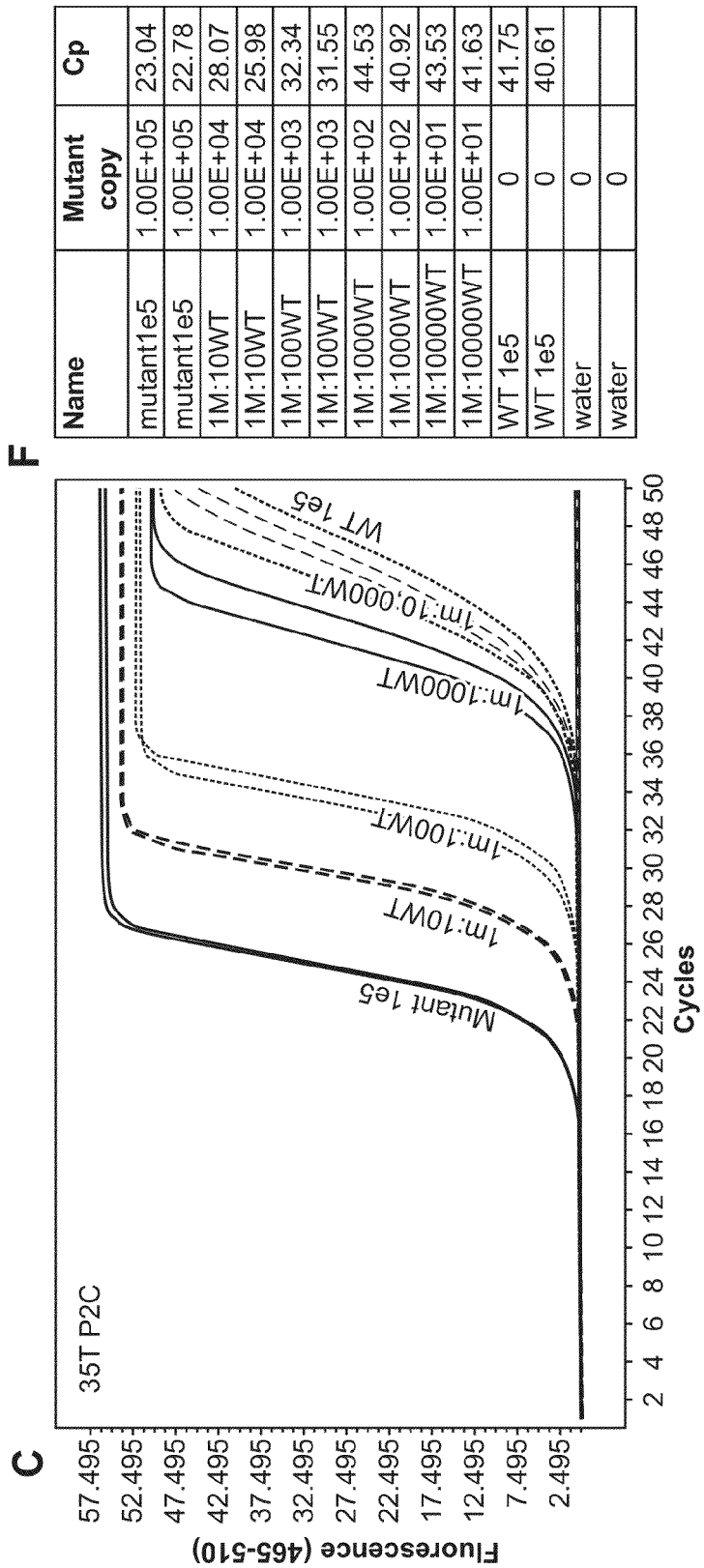
FIG. 6 (Cont. 2)

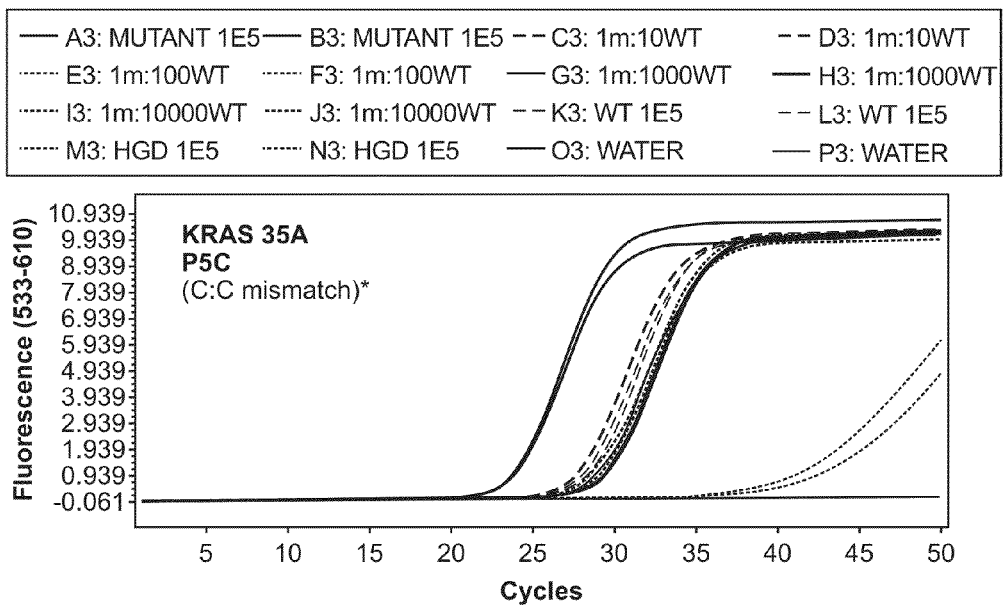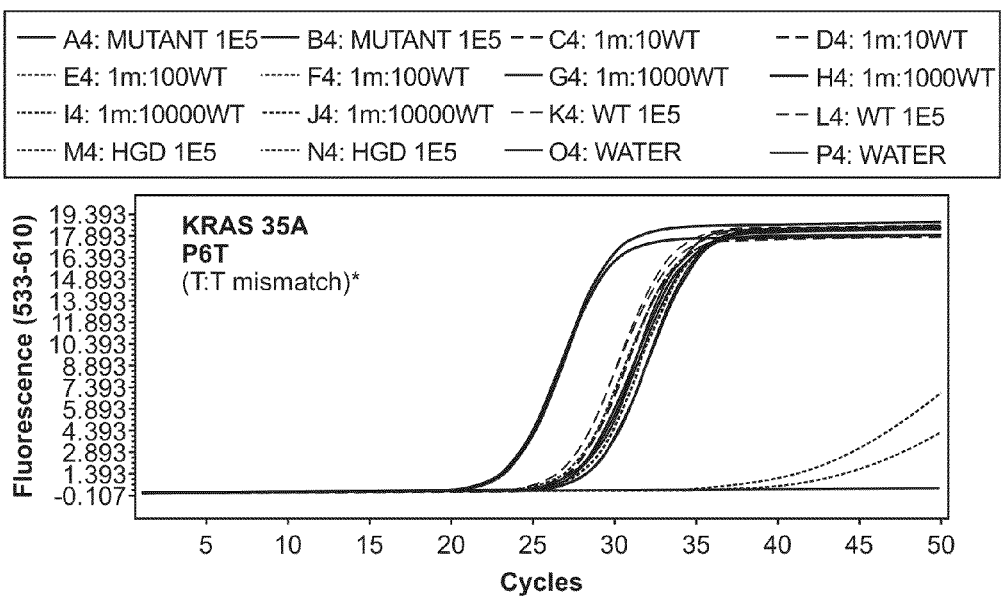
FIG. 7 (Cont. 1)

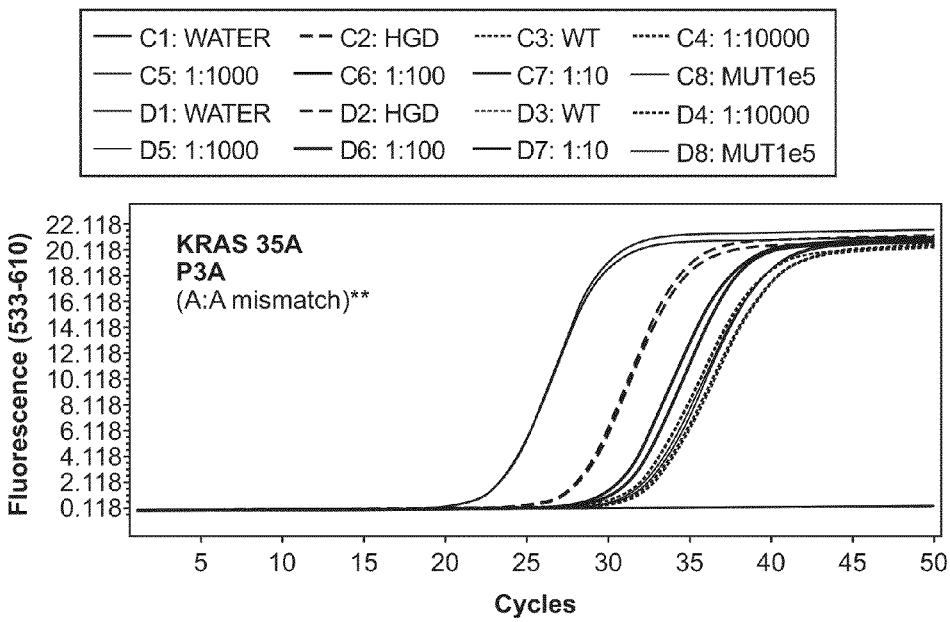
E
Amplification Curves
- C1: WATER
- C2: HGD
- C3: WT
- C4: 1:10000
- C5: 1:1000
- C6: 1:100
- C7: 1:10
- C8: MUT1e5
- D1: WATER
- D2: HGD
- D3: WT
- D4: 1:10000
- D5: 1:1000
- D6: 1:100
- D7: 1:10
- D8: MUT1e5
KRAS 35A P3A (A:A mismatch)**
F
| Name | Mutant copy | 35A P2C Cp | 35A P4A Cp | 35A P5C Cp | 35A P6T Cp | 35A P3A Cp |
|---|---|---|---|---|---|---|
| MUTANT1E5 | 1.00E+05 | 27.23 | 26.33 | 23.60 | 23.58 | 23.13 |
| MUTANT1E5 | 1.00E+05 | 27.08 | 26.42 | 23.61 | 23.35 | 23.16 |
| 1M:10WT | 1.00E+04 | 32.28 | 27.49 | 27.50 | 27.52 | 27.94 |
| 1M:10WT | 1.00E+04 | 31.73 | 26.96 | 27.35 | 26.82 | 27.87 |
| 1M:100WT | 1.00E+03 | 35.20 | 30.21 | 29.03 | 28.29 | 30.51 |
| 1M:100WT | 1.00E+03 | 35.71 | 29.54 | 28.92 | 27.27 | 31.04 |
| 1M:1000WT | 1.00E+02 | 38.70 | 30.89 | 29.28 | 28.73 | 32.16 |
| 1M:1000WT | 1.00E+02 | 38.83 | 30.90 | 28.79 | 27.78 | 32.46 |
| 1M:10000WT | 1.00E+01 | 40.46 | 30.89 | 29.17 | 28.65 | 32.62 |
| 1M:10000WT | 1.00E+01 | 40.64 | 30.74 | 28.47 | 28.10 | 32.78 |
| WT 1e5 | 0 | 40.52 | 29.96 | 28.22 | 27.94 | 31.89 |
| WT 1e5 | 0 | 39.81 | 30.16 | 27.86 | 26.88 | 31.81 |
| WATER | 0 |  |  |  |  | 39.35 |
| WATER | 0 |  |  | 45.00 |  | 19.83 |
FIG. 7 (Cont. 2)

SEQUENCE LISTING

<160> NUMBER OF SEQ ID NOS: 30

<210> SEQ ID NO 1
<211> LENGTH: 139
<212> TYPE: DNA
<213> ORGANISM: Artificial Sequence
<220> FEATURE:
<223> OTHER INFORMATION: KRAS wt fragment

<400> SEQUENCE: 1
cattattttt attataaggc ctgctgaaaa tgactgaata taaacttgtg gtagttggag     60
ctggtggcgt aggcaagagt gccttgacga tacagctaat tcagaatcat tttgtggacg    120
aatatgatcc aacaataga                                                  139

<210> SEQ ID NO 2
<211> LENGTH: 139
<212> TYPE: DNA
<213> ORGANISM: Artificial Sequence
<220> FEATURE:
<223> OTHER INFORMATION: KRAS G35A fragment

<400> SEQUENCE: 2
cattattttt attataaggc ctgctgaaaa tgactgaata taaacttgtg gtagttggag     60
ctgatggcgt aggcaagagt gccttgacga tacagctaat tcagaatcat tttgtggacg    120
aatatgatcc aacaataga                                                  139

<210> SEQ ID NO 3
<211> LENGTH: 20
<212> TYPE: DNA
<213> ORGANISM: Artificial Sequence
<220> FEATURE:
<223> OTHER INFORMATION: Synthetic primer

<400> SEQUENCE: 3
aggcctgctg aaaatgactg                                                  20

<210> SEQ ID NO 4
<211> LENGTH: 22
<212> TYPE: DNA
<213> ORGANISM: Artificial Sequence
<220> FEATURE:
<223> OTHER INFORMATION: Synthetic primer

<400> SEQUENCE: 4
ttgttggatc atattcgtcc ac                                               22

<210> SEQ ID NO 5
<211> LENGTH: 20
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 20
<223> OTHER INFORMATION: 3'-C6 hexanediol modified

<400> SEQUENCE: 5
cgccgaggat ggcgtaggca                                                  20

<210> SEQ ID NO 6
<211> LENGTH: 18
<212> TYPE: DNA

```
<213> ORGANISM: Artificial Sequence
<220> FEATURE:
<223> OTHER INFORMATION: Synthetic invasive oligonucleotide

<400> SEQUENCE: 6
tgtggtagtt ggagctgg                                                  18

<210> SEQ ID NO 7
<211> LENGTH: 33
<212> TYPE: DNA
<213> ORGANISM: Artificial Sequence
<220> FEATURE:
<223> OTHER INFORMATION: Synthetic FRET cassette
<220> FEATURE:
<221> NAME/KEY: misc_difference
<222> LOCATION: 1
<223> OTHER INFORMATION: 5'-Red Redmond Red fluorophore modified
<220> FEATURE:
<221> NAME/KEY: misc_difference
<222> LOCATION: 3
<223> OTHER INFORMATION: Quencher modified nucleotide
<220> FEATURE:
<221> NAME/KEY: misc_difference
<222> LOCATION: 33
<223> OTHER INFORMATION: 3'-C6 hexanediol modified

<400> SEQUENCE: 7
tcttcggcct tttggccgag agacctcggc gcg                                 33

<210> SEQ ID NO 8
<211> LENGTH: 139
<212> TYPE: DNA
<213> ORGANISM: Artificial Sequence
<220> FEATURE:
<223> OTHER INFORMATION: KRAS G35A fragment

<400> SEQUENCE: 8
cattattttt attataaggc ctgctgaaaa tgactgaata taaacttgtg gtagttggag     60
ctgatggcgt aggcaagagt gccttgacga tacagctaat tcagaatcat tttgtggacg    120
aatatgatcc aacaataga                                                 139

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
ttgtggtagt tggagctga                                                 19

<210> SEQ ID NO 10
<211> LENGTH: 22
<212> TYPE: DNA
<213> ORGANISM: Artificial Sequence
<220> FEATURE:
<223> OTHER INFORMATION: Synthetic primer

<400> SEQUENCE: 10
ctattgttgg atcatattcg tc                                             22

<210> SEQ ID NO 11
<211> LENGTH: 139
<212> TYPE: DNA
<213> ORGANISM: Artificial Sequence
<220> FEATURE:
<223> OTHER INFORMATION: KRAS G35A fragment
```

```
<400> SEQUENCE: 11
cattattttt attataaggc ctgctgaaaa tgactgaata taaacttgtg gtagttggag      60
ctgatggcgt aggcaagagt gccttgacga tacagctaat tcagaatcat tttgtggacg     120
aatatgatcc aacaataga                                                  139

<210> SEQ ID NO 12
<211> LENGTH: 139
<212> TYPE: DNA
<213> ORGANISM: Artificial Sequence
<220> FEATURE:
<223> OTHER INFORMATION: KRAS G35T fragment

<400> SEQUENCE: 12
cattattttt attataaggc ctgctgaaaa tgactgaata taaacttgtg gtagttggag      60
ctgttggcgt aggcaagagt gccttgacga tacagctaat tcagaatcat tttgtggacg     120
aatatgatcc aacaataga                                                  139

<210> SEQ ID NO 13
<211> LENGTH: 139
<212> TYPE: DNA
<213> ORGANISM: Artificial Sequence
<220> FEATURE:
<223> OTHER INFORMATION: KRAS G35C fragment

<400> SEQUENCE: 13
cattattttt attataaggc ctgctgaaaa tgactgaata taaacttgtg gtagttggag      60
ctgctggcgt aggcaagagt gccttgacga tacagctaat tcagaatcat tttgtggacg     120
aatatgatcc aacaataga                                                  139

<210> SEQ ID NO 14
<211> LENGTH: 19
<212> TYPE: DNA
<213> ORGANISM: Artificial Sequence
<220> FEATURE:
<223> OTHER INFORMATION: Synthetic primer

<400> SEQUENCE: 14
ttgtggtagt tggagatga                                                   19

<210> SEQ ID NO 15
<211> LENGTH: 19
<212> TYPE: DNA
<213> ORGANISM: Artificial Sequence
<220> FEATURE:
<223> OTHER INFORMATION: Synthetic primer

<400> SEQUENCE: 15
ttgtggtagt tggagatgt                                                   19

<210> SEQ ID NO 16
<211> LENGTH: 20
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 20
<223> OTHER INFORMATION: 3'-C6 hexanediol modified

<400> SEQUENCE: 16
cgccgaggtt ggcgtaggca                                                  20
```

```
<210> SEQ ID NO 17
<211> LENGTH: 19
<212> TYPE: DNA
<213> ORGANISM: Artificial Sequence
<220> FEATURE:
<223> OTHER INFORMATION: Synthetic primer

<400> SEQUENCE: 17
ttgtggtagt tggagatgc                                               19

<210> SEQ ID NO 18
<211> LENGTH: 20
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 20
<223> OTHER INFORMATION: 3'-C6 hexanediol modified

<400> SEQUENCE: 18
cgccgaggct ggcgtaggca                                              20

<210> SEQ ID NO 19
<211> LENGTH: 19
<212> TYPE: DNA
<213> ORGANISM: Artificial Sequence
<220> FEATURE:
<223> OTHER INFORMATION: Synthetic primer

<400> SEQUENCE: 19
ttgtggtagt tggagctaa                                               19

<210> SEQ ID NO 20
<211> LENGTH: 19
<212> TYPE: DNA
<213> ORGANISM: Artificial Sequence
<220> FEATURE:
<223> OTHER INFORMATION: Synthetic primer

<400> SEQUENCE: 20
ttgtggtagt tggagctct                                               19

<210> SEQ ID NO 21
<211> LENGTH: 21
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 21
<223> OTHER INFORMATION: 3'-C6 hexanediol modified

<400> SEQUENCE: 21
gacgcggaga tggcgtaggc a                                            21

<210> SEQ ID NO 22
<211> LENGTH: 21
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 21
<223> OTHER INFORMATION: 3'-C6 hexanediol modified
```

-continued

```
<400> SEQUENCE: 22
gacgcggagt tggcgtaggc a                                                 21

<210> SEQ ID NO 23
<211> LENGTH: 21
<212> TYPE: DNA
<213> ORGANISM: Artificial Sequence
<220> FEATURE:
<223> OTHER INFORMATION: Synthetic flap probe
<220> FEATURE:
<221> NAME/KEY: misc_difference
<222> LOCATION: 21
<223> OTHER INFORMATION: 3'-C6 hexanediol modified

<400> SEQUENCE: 23
gacgcggagc tggcgtaggc a                                                 21

<210> SEQ ID NO 24
<211> LENGTH: 35
<212> TYPE: DNA
<213> ORGANISM: Artificial Sequence
<220> FEATURE:
<223> OTHER INFORMATION: Synthetic FRET cassette
<220> FEATURE:
<221> NAME/KEY: misc_difference
<222> LOCATION: 1
<223> OTHER INFORMATION: 5'-FAM mdoified
<220> FEATURE:
<221> NAME/KEY: misc_difference
<222> LOCATION: 3
<223> OTHER INFORMATION: Quencher modified nucleotide
<220> FEATURE:
<221> NAME/KEY: misc_difference
<222> LOCATION: 35
<223> OTHER INFORMATION: 3'-C6 hexanediol modified

<400> SEQUENCE: 24
tctagccggt tttccggctg agactccgcg tccgt                                  35

<210> SEQ ID NO 25
<211> LENGTH: 19
<212> TYPE: DNA
<213> ORGANISM: Artificial Sequence
<220> FEATURE:
<223> OTHER INFORMATION: Synthetic probe

<400> SEQUENCE: 25
ttgtggtagt tggagctca                                                    19

<210> SEQ ID NO 26
<211> LENGTH: 22
<212> TYPE: DNA
<213> ORGANISM: Artificial Sequence
<220> FEATURE:
<223> OTHER INFORMATION: Synthetic probe

<400> SEQUENCE: 26
aacttgtggt agttggagat ga                                                22

<210> SEQ ID NO 27
<211> LENGTH: 20
<212> TYPE: DNA
<213> ORGANISM: Artificial Sequence
<220> FEATURE:
<223> OTHER INFORMATION: Synthetic probe

<400> SEQUENCE: 27
cttgtggtag ttggtgctga                                                   20
```

```
<210> SEQ ID NO 28
<211> LENGTH: 22
<212> TYPE: DNA
<213> ORGANISM: Artificial Sequence
<220> FEATURE:
<223> OTHER INFORMATION: Synthetic probe

<400> SEQUENCE: 28
aacttgtggt agttggacct ga                                            22

<210> SEQ ID NO 29
<211> LENGTH: 20
<212> TYPE: DNA
<213> ORGANISM: Artificial Sequence
<220> FEATURE:
<223> OTHER INFORMATION: Synthetic probe

<400> SEQUENCE: 29
cttgtggtag ttggagcaga                                               20

<210> SEQ ID NO 30
<211> LENGTH: 33
<212> TYPE: DNA
<213> ORGANISM: Artificial Sequence
<220> FEATURE:
<223> OTHER INFORMATION: Synthetic FRET cassette
<220> FEATURE:
<221> NAME/KEY: misc_difference
<222> LOCATION: 1
<223> OTHER INFORMATION: 5'-Redmond Red fluorophore modified
<220> FEATURE:
<221> NAME/KEY: misc_difference
<222> LOCATION: 3
<223> OTHER INFORMATION: Quencher modified nucleotide
<220> FEATURE:
<221> NAME/KEY: misc_difference
<222> LOCATION: 33
<223> OTHER INFORMATION: 3'-C6 hexanediol modified

<400> SEQUENCE: 30
tcttcggcct tttggccgag agacctcggc gcg                                33
```

MUTATION DETECTION ASSAY

BACKGROUND

Several point mutations in the human genome have a direct association with a disease. For example, several germline KRAS mutations have been found to be associated with Noonan syndrome (Schubbert et al. Nat. Genet. 2006 38: 331-6) and cardio-facio-cutaneous syndrome (Niihori et al. Nat. Genet. 2006 38: 294-6). Likewise, somatic KRAS mutations are found at high rates in leukemias, colorectal cancer (Burmer et al. Proc. Natl. Acad. Sci. 1989 86: 2403-7), pancreatic cancer (Almoguera et al. Cell 1988 53: 549-54) and lung cancer (Tam et al. Clin. Cancer Res. 2006 12: 1647-53). Many point mutations in the human genome have no apparent causative association with a disease.

Methods for the detection of point mutations may be used, for example, to provide a diagnostic for diseases that are associated with the point mutations.

SUMMARY

A method of sample analysis is provided. In certain embodiments, the method involves: a) amplifying a product from a sample that comprises both wild type copies of a genomic locus and mutant copies of the genomic locus that have a point mutation relative to said wild type copies of the genomic locus, to produce an amplified sample, where: i. the amplifying is done using a first primer and a second primer; and ii. the first primer comprises a 3' terminal nucleotide that base pairs with point mutation and also comprises a nucleotide sequence that is fully complementary to a sequence in the locus with the exception of a single base mismatch within 6 bases of the 3' terminal nucleotide; and b) detecting the presence of said product in said amplified sample using a flap assay that employs an invasive oligonucleotide. A kit for performing the method is also provided.

DEFINITIONS

Figure 1:
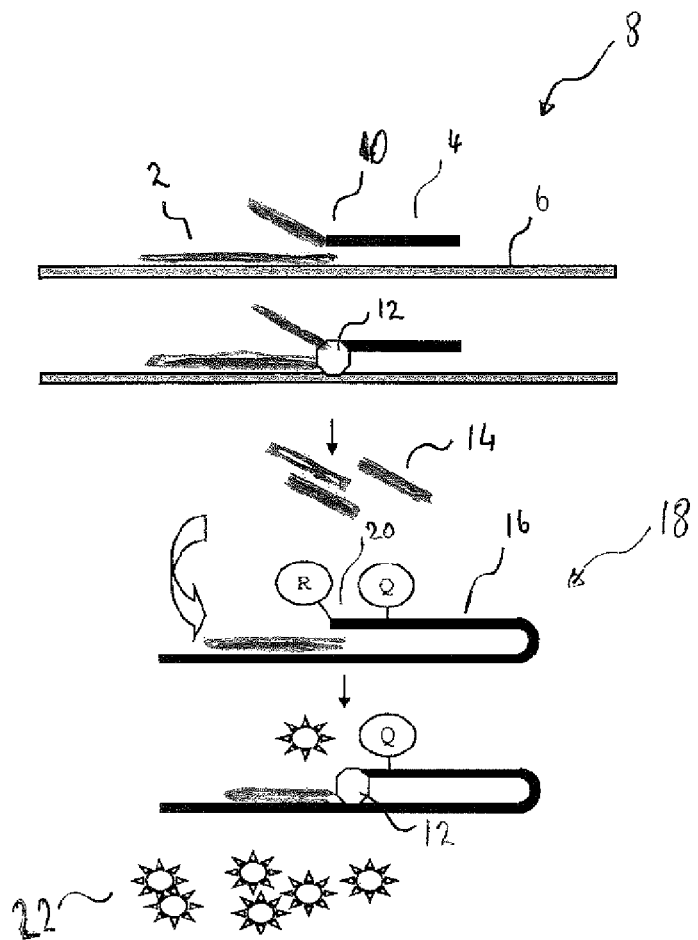
FIG. 1 schematically illustrates some of the general principles of a flap assay.

The term "sample" as used herein relates to a material or mixture of materials, typically, although not necessarily, in liquid form, containing one or more analytes of interest.

The term "nucleotide" is intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the term "nucleotide" includes those moieties that contain hapten or fluorescent labels and may contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the likes.

The term "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions. Naturally-occurring nucleotides include guanine, cytosine, adenine and thymine (G, C, A and T, respectively).

The term "nucleic acid sample," as used herein denotes a sample containing nucleic acid.

The term "target polynucleotide," as used herein, refers to a polynucleotide of interest under study. In certain embodiments, a target polynucleotide contains one or more target sites that are of interest under study.

The term "oligonucleotide" as used herein denotes a single stranded multimer of nucleotides of from about 2 to 200 nucleotides. Oligonucleotides may be synthetic or may be made enzymatically, and, in some embodiments, are 10 to 50 nucleotides in length. Oligonucleotides may contain ribonucleotide monomers (i.e., may be oligoribonucleotides) or deoxyribonucleotide monomers. An oligonucleotide may be 10 to 20, 11 to 30, 31 to 40, 41 to 50, 51 to 60, 61 to 70, 71 to 80, 80 to 100, 100 to 150 or 150 to 200 nucleotides in length, for example.

The term "duplex," or "duplexed," as used herein, describes two complementary polynucleotides that are base-paired, i.e., hybridized together.

The term "primer" as used herein refers to an oligonucleotide that has a nucleotide sequence that is complementary to a region of a target polynucleotide. A primer binds to the complementary region and is extended, using the target nucleic acid as the template, under primer extension conditions. A primer may be in the range of about 15 to about 50 nucleotides although primers outside of this length may be used. A primer can be extended from its 3' end by the action of a polymerase. An oligonucleotide that cannot be extended from it 3' end by the action of a polymerase is not a primer.

The term "extending" as used herein refers to any addition of one or more nucleotides to the end of a nucleic acid, e.g. by ligation of an oligonucleotide or by using a polymerase.

The term "amplifying" as used herein refers to generating one or more copies of a target nucleic acid, using the target nucleic acid as a template.

The term "denaturing," as used herein, refers to the separation of a nucleic acid duplex into two single strands.

The terms "determining", "measuring", "evaluating", "assessing," "assaying," "detecting," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end.

As used herein, the term "$T_m$" refers to the melting temperature of an oligonucleotide duplex at which half of the duplexes remain hybridized and half of the duplexes dissociate into single strands. The $T_m$ of an oligonucleotide duplex may be experimentally determined or predicted using the following formula $T_m=81.5+16.6(\log_{10}[Na^+])+0.41$ (fraction G+C)−(60/N), where N is the chain length and [$Na^+$] is less than 1 M. See Sambrook and Russell (2001; Molecular Cloning: A Laboratory Manual, $3^{rd}$ ed., Cold Spring Harbor Press, Cold Spring Harbor N.Y., ch. 10). Other formulas for predicting $T_m$ of oligonucleotide duplexes exist and one formula may be more or less appropriate for a given condition or set of conditions.

As used herein, the term "$T_m$-matched" refers to a plurality of nucleic acid duplexes having $T_m$s that are within a defined range, e.g., within 5° C. or 10° C. of each other.

As used herein, the term "reaction mixture" refers to a mixture of reagents that are capable of reacting together to produce a product in appropriate external conditions over a period of time. A reaction mixture may contain PCR reagents and flap cleavage reagents, for example, the recipes for which are independently known in the art.

The term "mixture", as used herein, refers to a combination of elements, that are interspersed and not in any particular order. A mixture is heterogeneous and not spatially separable into its different constituents. Examples of mixtures of elements include a number of different elements that are dissolved in the same aqueous solution, or a number of different elements attached to a solid support at random or in no particular order in which the different elements are not spatially distinct. A mixture is not addressable. To illustrate by example, an array of spatially separated surface-bound polynucleotides, as is commonly known in the art, is not a mixture of surface-bound polynucleotides because the species of surface-bound polynucleotides are spatially distinct and the array is addressable.

As used herein, the term "PCR reagents" refers to all reagents that are required for performing a polymerase chain reaction (PCR) on a template. As is known in the art, PCR reagents essentially include a first primer, a second primer, a thermostable polymerase, and nucleotides. Depending on the polymerase used, ions (e.g., $Mg^{2+}$) may also be present. PCR reagents may optionally contain a template from which a target sequence can be amplified.

As used herein, the term "flap assay" refers to an assay in which a flap oligonucleotide is cleaved in an overlap-dependent manner by a flap endonuclease to release a flap that is then detected. The principles of flap assays are well known and described in, e.g., Lyamichev et al. (Nat. Biotechnol. 1999 17:292-296), Ryan et al (Mol. Diagn. 1999 4:135-44) and Allawi et al (J Clin Microbiol. 2006 44: 3443-3447). For the sake of clarity, certain reagents that are employed in a flap assay are described below. The principles of a flap assay are illustrated in FIG. 1. In the flap assay shown in FIG. 1, an invasive oligonucleotide 2 and flap oligonucleotide 4 are hybridized to target 6 to produce a first complex 8 that contains a nucleotide overlap at position 10. First complex 8 is a substrate for flap endonuclease. Flap endonuclease 12 cleaves flap oligonucleotide 4 to release a flap 14 that hybridizes with FRET cassette 16 that contains a quencher "Q" and a nearby quenched fluorophore "R" that is quenched by the quencher Q. Hybridization of flap 14 to FRET cassette 16 results in a second complex 18 that contains a nucleotide overlap at position 20. The second complex is also a substrate for flap endonuclease. Cleavage of FRET cassette 16 by flap endonuclease 12 results in release of the fluorophore 22, which produces a fluorescent signal. These components are described in greater detail below.

As used herein, the term "invasive oligonucleotide" refers to an oligonucleotide that is complementary to a region in a target nucleic acid. The 3' terminal nucleotide of the invasive oligonucleotide may or may not base pair a nucleotide in the target (e.g., which may be the site of a SNP or a mutation, for example).

As used herein, the term "flap oligonucleotide" refers to an oligonucleotide that contains a flap region and a region that is complementary to a region in the target nucleic acid. The target complementary regions on the invasive oligonucleotide and the flap oligonucleotide overlap by a single nucleotide such that, when they are annealed to the target nucleic acid, the complementary sequences overlap. As is known, if: a) the 3' terminal nucleotide of the invasive nucleotide and b) the nucleotide that overlaps with that nucleotide in the flap oligonucleotide both base pair with a nucleotide in the target nucleic acid, then a particular structure is formed. This structure is a substrate for an enzyme, defined below as a flap endonuclease, that cleaves the flap from the target complementary region of the flap oligonucleotide. If the 3' terminal nucleotide of the invasive oligonucleotide does not base pair with a nucleotide in the target nucleic acid, or if the overlap nucleotide in the flap oligononucleotide does not base pair with a nucleotide in the target nucleic acid, the complex is not a substrate for the enzyme and there is little or no cleavage.

The term "flap endonuclease" or "FEN" for short, as used herein, refers to a class of nucleolytic enzymes that act as structure specific endonucleases on DNA structures with a duplex containing a single stranded 5' overhang, or flap, on one of the strands that is displaced by another strand of nucleic acid, i.e., such that there are overlapping nucleotides at the junction between the single and double-stranded DNA. FENs catalyze hydrolytic cleavage of the phosphodiester bond at the junction of single and double stranded DNA, releasing the overhang, or the flap. Flap endonucleases are reviewed by Ceska and Savers (*Trends Biochem. Sci.* 1998 23:331-336) and Liu et al (*Annu. Rev. Biochem.* 2004 73: 589-615). FENs may be individual enzymes, multi-subunit enzymes, or may exist as an activity of another enzyme or protein complex, e.g., a DNA polymerase. A flap endonuclease may be thermostable.

As used herein, the term "cleaved flap" refers to a single-stranded oligonucleotide that is a cleavage product of a flap assay.

As used herein, the term "FRET cassette" refers to a hairpin oligonucleotide that contains a fluorophore moiety and a nearby quencher moiety that quenches the fluorophore. Hybridization of a cleaved flap with a FRET cassette produces a secondary substrate for the flap endonuclease. Once this substrate is formed, the 5' fluorophore-containing base is cleaved from the cassette, thereby generating a fluorescence signal.

As used herein, the term "flap assay reagents" refers to all reagents that are required for performing a flap assay on a substrate. As is known in the art, flap assays include an invasive oligonucleotide, a flap oligonucleotide, a flap endonuclease and a FRET cassette, as described above. Flap assay reagents may optionally contain a target to which the invasive oligonucleotide and flap oligonucleotide bind.

As used herein, the term "genomic locus" refers to a defined region in a genome. A genomic locus exists at the same location in the genomes of different cells from the same individual, or in different individuals. A genomic locus in one cell or individual may have a nucleotide sequence that is identical or very similar (i.e., more than 99% identical) to the same genomic locus in a different cell or individual. The difference in nucleotide sequence between the same locus in different cells or individuals may be due to one or more nucleotide substitutions. A SNP (single nucleotide polymorphism) is one type of point mutation that occurs at the same genomic locus between different individuals in a population. Point mutations may be somatic in that they occur between different cells in the same individual. A genomic locus mutation may be defined by genomic coordinates, by name, or using a symbol.

As used herein, a "site of a mutation" refers to the position of a nucleotide substitution in a genomic locus. Unless otherwise indicated, the site of a mutation in a nucleic acid can have a mutant allele or wild type allele of a mutation. The site of a mutation may be defined by genomic coordinates, or coordinates relative to the start codon of a gene (e.g., in the case of the "KRAS G35T mutation").

As used herein, the term "point mutation" refers to the identity of the nucleotide present at a site of a mutation in the mutant copy of a genomic locus. The nucleotide may be on either strand of a double stranded DNA molecule.

As used herein, the term "wild type", with reference a genomic locus, refers to the alleles of a locus that contain a wild type sequence. In the case of locus containing a SNP, the wild type sequence may contain the predominant allele of the SNP.

As used herein, the term "mutant", with reference to a genomic locus, refers to the alleles of a locus that contain a mutant sequence. In the case of a locus containing a SNP, the mutant sequence may contain a minor allele of the SNP. The mutant allele of a genomic locus may contain a nucleotide substitution that is not silent in that it that either alters the expression of a protein or changes the amino acid sequence of a protein, which causes a phenotypic change (e.g., a cancer-related phenotype) in the cells that are heterozygous or homozygous for the mutant sequence relative to cells containing the wild type sequence. Alternatively, the mutant allele of a genomic locus may contain a nucleotide substitution that is silent.

As used herein, the term "corresponds to" and grammatical equivalents thereof in the context of, for example, a nucleotide in an oligonucleotide that corresponds to a site of a mutation, is intended to identify the nucleotide that is correspondingly positioned relative to (i.e., positioned across from) a site of a mutation when two nucleic acids (e.g., an oligonucleotide and genomic DNA containing the mutation) are hybridized. Again, unless otherwise indicated (e.g., in the case of a nucleotide that "does not base pair" or "base pairs" with a point mutation) a nucleotide that corresponds to a site of a mutation may base pair with either the mutant or wild type allele of a sequence.

A sample that comprises "both wild type copies of a genomic locus and mutant copies of the genomic locus" and grammatical equivalents thereof, refers to a sample that contains multiple DNA molecules of the same genomic locus, where the sample contains both wild type copies of the genomic locus (which copies contain the wild type allele of the locus) and mutant copies of the same locus (which copies contain the mutant allele of the locus). In this context, the term "copies" is not intended to mean that the sequences were copied from one another. Rather, the term "copies" in intended to indicate that the sequences are of the same locus in different cells or individuals.

As used herein the term "nucleotide sequence" refers to a contiguous sequence of nucleotides in a nucleic acid. As would be readily apparent, number of nucleotides in a nucleotide sequence may vary greatly. In particular embodiments, a nucleotide sequence (e.g., of an oligonucleotide) may be of a length that is sufficient for hybridization to a complementary nucleotide sequence in another nucleic acid. In these embodiments, a nucleotide sequence may be in the range of at least 10 to 50 nucleotides, e.g., 12 to 20 nucleotides in length, although lengths outside of these ranges may be employed in many circumstances.

As used herein the term "fully complementary to" in the context of a first nucleic acid that is fully complementary to a second nucleic acid refers to a case when every nucleotide of a contiguous sequence of nucleotides in a first nucleic acid base pairs with a complementary nucleotide in a second nucleic acid. As will be described below, a nucleic acid may be fully complementary to another sequence "with the exception of a single base mismatch", meaning that the sequences are otherwise fully complementary with the exception of a single base mismatch (i.e., a single nucleotide that does not base pair with the corresponding nucleotide in the other nucleic acid).

As used herein the term a "primer pair" is used to refer to two primers that can be employed in a polymerase chain reaction to amplify a genomic locus. A primer pair may in certain circumstances be referred to as containing "a first primer" and "a second primer" or "a forward primer" and "a reverse primer". Use of any of these terms is arbitrary and is not intended to indicate whether a primer hybridizes to a top strand or bottom strand of a double stranded nucleic acid.

The nucleotides of an oligonucleotide may be designated by their position relative to the 3' terminal nucleotide of an oligonucleotide. For example, the nucleotide immediately 5' to the 3' terminal nucleotide of an oligonucleotide is at the "−1" position, the nucleotide immediately 5' to the nucleotide at the −1 position is the "−2" nucleotide, and so on. Nucleotides that are "within 6 bases" of a 3' terminal nucleotide are at the −1, −2, −3, −4, −5 and −6 positions relative to the 3' terminal nucleotide.

DESCRIPTION OF EXEMPLARY EMBODIMENTS

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In the following description, the skilled artisan will understand that any of a number of polymerases and flap endonucleases could be used in the methods, including without limitation, those isolated from thermostable or hyperthermostable prokaryotic, eukaryotic, or archaeal organisms. The skilled artisan will also understand that the enzymes that are used in the method, e.g., polymerase and flap endonuclease, include not only naturally occurring enzymes, but also recombinant enzymes that include enzymatically active fragments, cleavage products, mutants, and variants of wild type enzymes.

In further describing the method, the reagent mixture used in the method will be described first, followed by a description of the reaction conditions that may be used in the method.

Reaction Mixture

The reaction mixture used in the method generally contains: a) amplification reagents that are sufficient to amplify a target genomic locus from a nucleic acid sample, where one of the primers used for amplification comprises a 3' terminal nucleotide that base pairs with a point mutation in the genomic locus and also comprises a nucleotide sequence that is fully complementary to a sequence in the locus with the exception of a single base mismatch within 6 bases of the 3' terminal nucleotide; b) flap assay reagents comprising a flap endonuclease and a FRET cassette; c) the nucleic acid sample. The reaction mixture is characterized in that it can amplify and detect the presence of mutant copies of a genomic locus in a background of wild type copies of the locus in the sample.

Specifically, the reaction mixture used in the method may contain: a) amplification reagents comprising a thermostable polymerase, nucleotides (e.g., dGTP, dATP, dTTP and dCTP), reaction buffer (which includes $Mg^{2+}$), a first primer, and a second primer for amplifying a target genomic locus from a nucleic acid sample; wherein the first primer: i. comprises a 3' terminal nucleotide that base pairs with a point mutation in the genomic locus; and ii. comprises a nucleotide sequence that is fully complementary to a sequence in the locus with the exception of a single base mismatch within 6 bases of the 3' terminal nucleotide; b) flap assay reagents comprising a flap endonuclease, a FRET cassette and a flap oligonucleotide that comprises a nucleotide that base pairs with said point mutation; and c) the nucleic acid sample, wherein the nucleic acid sample comprises both wild type copies of the genomic locus and mutant copies of the genomic locus that have a point mutation relative to the wild type copies of the genomic locus. The reaction mixture is characterized in that it can amplify and detect the presence of said mutant copies of the genomic locus in the sample.

In certain embodiments and as will be described in greater detail below, the first primer of the amplification reagents may be employed as an invasive primer in the flap assay reagents. In other embodiments, however, the reaction mixture may optionally contain, an invasive oligonucleotide that is distinct from the first primer that has a 3' terminal nucleotide that base pairs with the point mutation. Therefore, depending on how the assay is performed (i.e., depending on whether one of the PCR primers is used as an invasive oligonucleotide in the flap assay) the reaction mix may additionally contain an invasive oligonucleotide that is distinct from the PCR primers.

The exact identities and concentrations of the reagents present in the reaction mixture may be similar to or the same as those independently employed in PCR and flap cleavage assays, with the exception that the reaction mixture contains $Mg^{2+}$ at a concentration that is higher than employed in conventional PCR reaction mixtures (which contain $Mg^{2+}$ at a concentration of between about 1.8 mM and 3 mM). In certain embodiments, the reaction mixture described herein contains $Mg^{2+}$ at a concentration of in the range of 4 mM to 10 min, e.g., 6 mM to 9 mM. Exemplary reaction buffers and DNA polymerases that may be employed in the subject reaction mixture include those described in various publications (e.g., Ausubel, et al., Short Protocols in Molecular Biology, 3rd ed., Wiley & Sons 1995 and Sambrook et al., Molecular Cloning: A Laboratory Manual, Third Edition, 2001 Cold Spring Harbor, N.Y.). Reaction buffers and DNA polymerases suitable for PCR may be purchased from a variety of suppliers, e.g., Invitrogen (Carlsbad, Calif.), Qiagen (Valencia, Calif.) and Stratagene (La Jolla, Calif.). Exemplary polymerases include Taq, Pfu, Pwo, UlTma and Vent, although many other polymerases may be employed in certain embodiments. Guidance for the reaction components suitable for use with a polymerase as well as suitable conditions for their use is found in the literature supplied with the polymerase. Primer design is described in a variety of publications, e.g., Diffenbach and Dveksler (PCR Primer, A Laboratory Manual, Cold Spring Harbor Press 1995); R. Rapley, (The Nucleic Acid Protocols Handbook (2000), Humana Press, Totowa, N.J.); Schena and Kwok et al., Nucl. Acid Res. 1990 18:999-1005). Primer and probe design software programs are also commercially available, including without limitation, Primer Detective (ClonTech, Palo Alto, Calif.), Lasergene, (DNASTAR, Inc., Madison, Wis.); and Oligo software (National Biosciences, Inc., Plymouth, Minn.) and iOligo (Caesar Software, Portsmouth, N.H.).

Exemplary flap cleavage assay reagents are found in Lyamichev et al. (Nat. Biotechnol. 1999 17:292-296), Ryan et al (Mol. Diagn. 1999 4:135-44) and Allawi et al (J Clin Microbiol. 2006 44: 3443-3447). Appropriate conditions for flap endonuclease reactions are either known or can be readily determined using methods known in the art (see, e.g., Kaiser et al., J. Biol. Chem. 274:21387-94, 1999). Exemplary flap endonucleases that may be used in the method include, without limitation, *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1, *Methanobacterium thermoautotrophicum* FEN-1, *Thermus thermophilus* FEN-1, CLEAVASE™ (Third Wave, Inc., Madison, Wis.), *S. cerevisiae* RTH1, *S. cerevisiae* RAD27, *Schizosaccharomyces pombe* rad2, bacteriophage T5 5'-3' exonuclease, *Pyroccus horikoshii* FEN-1, human exonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of cleaving enzymes can be found in, among other places, Lyamichev et al., Science 260:778-83, 1993; E is et al., Nat. Biotechnol. 19:673-76, 2001; Shen et al., Trends in Bio. Sci. 23:171-73, 1998; Kaiser et al. J. Biol. Chem. 274:21387-94, 1999; Ma et al., J. Biol. Chem. 275:24693-700, 2000; Allawi et al., J. Mol. Biol. 328:537-54, 2003; Sharma et al., J. Biol. Chem. 278:23487-96, 2003; and Feng et al., Nat. Struct. Mol. Biol. 11:450-56, 2004.

In particular embodiments, the reaction mix may contain reagents for assaying multiple (e.g., at least 2, 3, 4 or more) different targets sequences in parallel. In these cases, the reaction mix may contain multiple pairs of PCR primers, multiple different flap oligonucleotides having different flaps, and multiple different FRET cassettes for detecting the different flaps, once they are cleaved. In one embodiment, oligonucleotides in a mixture may have common flaps but different binding sequences to allow for, for example, a set of mutations to cleave a common FRET cassette and report a signal where a single fluorophore is indicative of the presence of a mutation. In this embodiment, which mutation is present in the sample may be determined after the presence of a mutation has identified. Optionally, the reaction may contain multiple invasive oligonucleotides if one of the PCR primers is not used as an invasive oligonucleotide. Upon cleavage of the FRET cassettes, multiple distinguishable fluorescent signals may be observed. The fluorophore may be selected from, e.g., 6-carboxyfluorescein (FAM), which has excitation and emission wavelengths of 485 nm and 520 nm respectively, Redmond Red, which has excitation and emission wavelengths of 578 nm and 650 nm respectively and Yakima Yellow, which has excitation and emission wavelengths of 532 nm and 569 nm respectively, and Quasor670 which has excitation and emission wavelengths of 644 nm and 670 nm respectively, although many others could be employed. In certain cases, at least one of the PCR primer pairs, flap oligonucleotides and FRET cassettes may be for the detection of an internal control.

As noted above, one of the PCR primers (arbitrarily designated as the "first" primer), comprises a 3' terminal nucleotide that base pairs with a point mutation (i.e., the mutant allele) in the genomic locus and also comprises a nucleotide sequence that is fully complementary to a sequence in the locus with the exception of a single base mismatch within 6 bases of the 3' terminal nucleotide (e.g., at the −1 position, the −2 position, the −3 position, the −4 position, the −5 position or the −6 position, relative to the 3' terminal nucleotide). In other words, in addition to having a 3' terminal nucleotide that base pairs with only the mutant allele of the mutation in the genomic locus, the primer also has a destabilizing mismatch near the 3' end that neither bases pairs with the mutant allele or the wild type allele of the genomic region. Without being limited to any particular theory, the destabilizing mismatch is believed to destabilize hybridization of the 3' end of the first primer to the wild-type sequence to a greater extend than mutant sequence, thereby resulting in preferential amplification of the mutant sequence. As will be described in greater detail below, the presence of the product amplified using the first and second primers may be detected using a flap assay that employs the first primer or another oligonucleotide that has the destabilizing mutation and a terminal nucleotide that base pairs with only the mutant allele at the genomic locus. The use of such a sequence (i.e., a sequence that contains the destabilizing mutation and a terminal nucleotide that base pairs with only the mutant allele at the genomic locus) in the detection step provides further discrimination between mutant and wild type sequences in the amplification products. Without being bound to any particular theory, it is believed that the discrimination between mutant and wild type largely occurs in the first few rounds of amplification since the amplified sequence (i.e., the amplicon) provides a perfectly complementary sequence for the PCR primers to hybridize to. The wild type sequence should not be amplified, whereas the mutant sequence should be efficiently amplified.

The destabilizing mismatch can be done by substituting a nucleotide that base pairs with the point mutation with another nucleotide. The nucleotide that is substituted into the sequence may be another natural nucleotide (e.g., dG, dA, dT or dC), or, in certain circumstances, a modified nucleotide. In certain embodiments, the 3' end of the first primer may contain more than 1, e.g., 2 or 3, mismatches. In particular embodiments, the type of mismatch (e.g., whether the mismatch is a G:T mismatch or a C:T mismatch, etc.) used affects a primer's ability to discriminate between wild type and mutant sequences. In general terms, the order of the stabilities (from most stable to least stable) of various mismatches are as follows: G:T>G:G=A:G>T:G>G:A=T:T>T:C>A:C>C:T>A:A>C:A>C:C (as described in Gaffney and Jones (Biochemistry 1989 26: 5881-5889)), although the basepairs that surround the mismatch can affect this order in certain circumstances (see, e.g., Ke et al Nucleic Acids Res. 1993 21:5137-5143). The mismatch used may be optimized experimentally to provide the desired discrimination.

As would be apparent, the various oligonucleotides used in the method are designed so as to not interfere with each other. For example, in particular embodiments, the flap oligonucleotide may be capped at its 3' end, thereby preventing its extension. Likewise, in certain embodiments, the invasive oligonucleotide may also be capped at its 3' end if it is not used as one of the PCR primers. In particular embodiment, if the invasive oligonucleotide is not used as one of the PCR primers, then the invasive oligonucleotide may be present at a concentration that is in the range of 5% to 50%, e.g., 10% to 40% of the concentration of the PCR primers. Further, in certain cases, the $T_m$s of the flap portion and the target complementary regions of the flap oligonucleotide may independently be at least 10° C. lower (e.g., 10-20° C. lower) than the $T_m$s of the PCR primers, which results in a) less hybridization of the flap oligonucleotide to the target nucleic acid at higher temperatures (65° C. to 75° C.) and b) less hybridization of any cleaved flap to the FRET cassette at higher temperatures (65° C. to 75° C.), thereby allowing the genomic locus to be amplified by PCR at a temperature at which the flap does not efficiently hybridize.

In a multiplex reaction, the primers may be designed to have similar thermodynamic properties, e.g., similar $T_m$s, G/C content, hairpin stability, and in certain embodiments may all be of a similar length, e.g., from 18 to 30 nt, e.g., 20 to 25 nt in length. The other reagents used in the reaction mixture may also be $T_m$ matched.

The assay mixture may be present in a vessel, including without limitation, a tube; a multi-well plate, such as a 96-well, a 384-well, a 1536-well plate; and a microfluidic device. In certain embodiments, multiple multiplex reactions are performed in the same reaction vessel. Depending on how the reaction is performed, the reaction mixture may be of a volume of 5 µl to 200 µl, e.g., 10 µl to 100 µl, although volumes outside of this range are envisioned.

In certain embodiments, a subject reaction mix may further contain a nucleic acid sample. In particular embodiments, the sample may contain genomic DNA or an amplified version thereof (e.g., genomic DNA amplified using the methods of Lage et al, Genome Res. 2003 13: 294-307 or published patent application US20040241658, for example). In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the genomic sample may be from a formalin fixed paraffin embedded (FFPE) sample.

In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human, and it may be processed prior to use in the subject assay. For example, the nucleic acid may be extracted from the sample prior to use, methods for which are known.

For example, DNA can be extracted from stool from any number of different methods, including those described in, e.g., Coll et al (J. of Clinical Microbiology 1989 27: 2245-2248), Sidransky et al (Science 1992 256: 102-105), Villa (Gastroenterology 1996 110: 1346-1353) and Nollau (BioTechniques 1996 20: 784-788), and U.S. Pat. Nos. 5,463,782, 7,005,266, 6,303,304 and 5,741,650. Commercial DNA extraction kits for the extraction of DNA from stool include the QIAamp stool mini kit (QIAGEN, Iden, Germany), Instagene Matrix (Bio-Rad, Hercules, Calif.), and RapidPrep Micro Genomic DNA isolation kit (Pharmacia Biotech Inc., Piscataway, N.J.), among others.

Method for Sample Analysis

In performing the subject method, the reaction mixture described above may be subjected to one or more sets for thermocycling conditions. Exemplary conditions include, for example those described in Allawi et al (J Clin Microbiol. 2006 44: 3443-3447). In one embodiment, the reaction mixture may be subjected to conventional PCR thermocycling (i.e., multiple rounds of denaturation at a temperature of over 90° C., e.g., at about 95° C., annealing at a temperature of 65° C. to 75° C. and extension at a temperature of 65° C. to 75° C.) followed by a period at high temperature to denature the themostable polymerase (e.g., about 99° C.), and then a period at a temperature that is about 10° C. below the extension temperature during which fluorescence is detected.

In other embodiments, the reaction mixture may be subject to cycling conditions in which an increase in the amount of amplified product (indicated by the amount of fluorescence) can be measured in real-time, where the term "real-time" is intended to refer to a measurement that is taken as the reaction progresses and products accumulate. The measurement may be expressed as an absolute number of copies or a relative amount when normalized to a control nucleic acid in the sample. In one real time embodiment, the reaction may be subjected to the thermocycling conditions described in, e.g., Tadokoro (J. Vir. Methods 2009 155: 182-186). In this embodiment, the reaction mixture may be subjected to multiple cycles of four steps that include a denaturation step at a temperature of over 90° C., e.g., at about 95° C., annealing at a temperature in the range of 61° C. to 69° C., flap cleavage at a temperature of 50° C., and extension at a temperature of 72° C. In this embodiment, fluorescence can be monitored in each cycle to provide a real time measurement of the amount of product that is accumulating in the reaction mixture.

In an alternative embodiment, the reaction mixture may be subjected to the following thermocycling conditions: a first set of 5 to 15 (e.g., 8 to 12) cycles of: i. a first temperature of at least 90° C.; ii. a second temperature in the range of 60° C. to 75° C. (e.g., 65° C. to 75° C.); iii. a third temperature in the range of 65° C. to 75° C.; followed by: a second set of 20-50 cycles of: i. a fourth temperature of at least 90° C.; ii. a fifth temperature that is at least 10° C. lower than the second temperature (e.g., in the range of 50° C. to 55° C.); and iii. a sixth temperature in the range of 65° C. to 75° C. No additional reagents need to be added to the reaction mixture during the thermocycling, e.g., between the first and second sets of cycles. In particular embodiments, the thermostable polymerase is not inactivated between the first and second sets of conditions, thereby allowing the target to be amplified during each cycle of the second set of cycles. In particular embodiments, the second and third temperatures are the same temperature such that "two step" thermocycling conditions are performed. Each of the cycles may be independently of a duration in the range of 10 seconds to 3 minutes, although durations outside of this range are readily employed. In each cycle of the second set of cycles (e.g., while the reaction is in the fifth temperature), a signal generated by cleavage of the flap probe may be measured to provide a real-time measurement of the amount of target nucleic acid in the sample.

Figure 2:
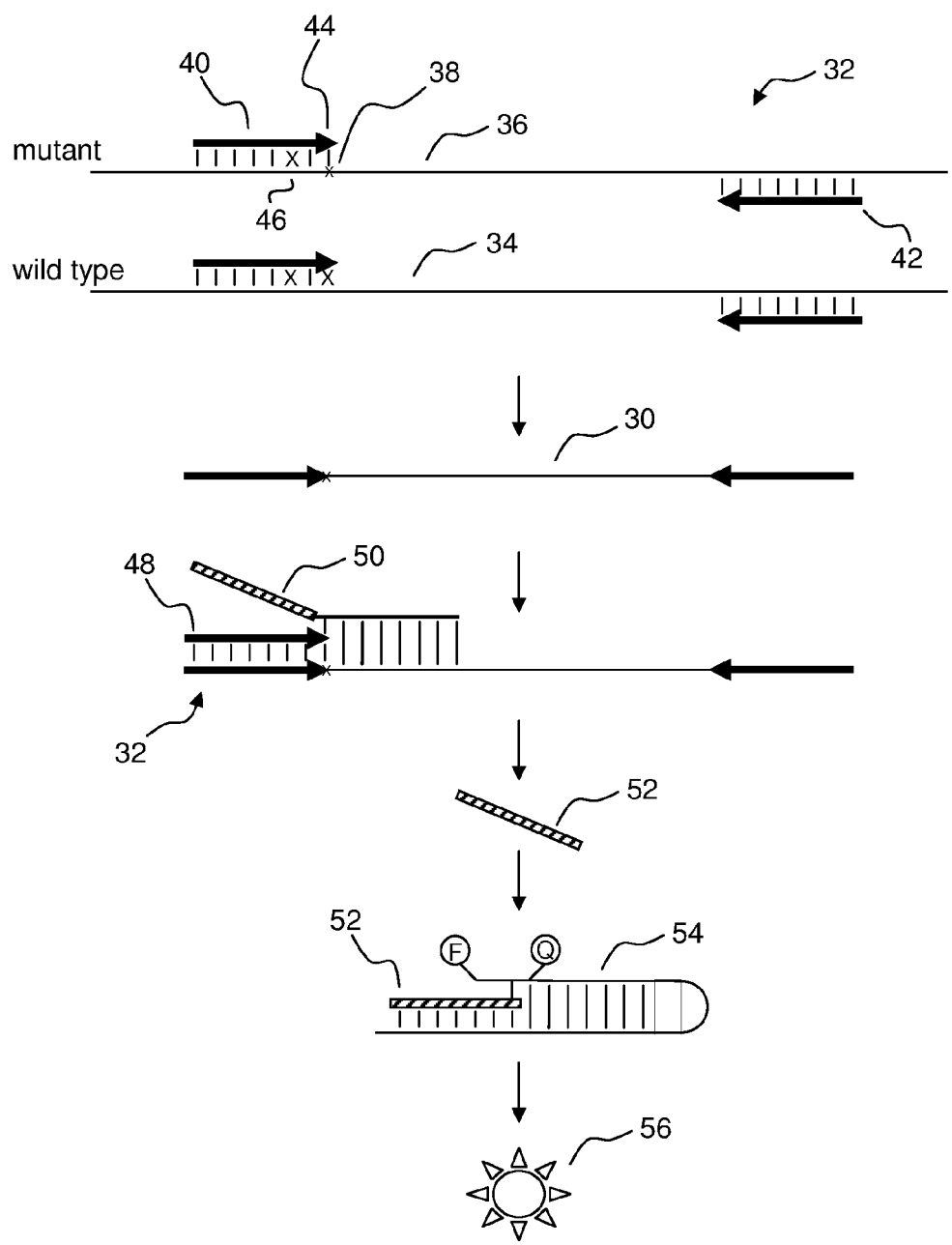
FIG. 2 schematically illustrates one embodiment of the subject method.

Some of the principles of the subject of sample analysis method are schematically illustrated in FIG. 2. With reference to FIG. 2, the method includes amplifying product 30 from sample 32 that comprises both wild type copies of a genomic locus 34 and mutant copies of the genomic locus 36 that have a point mutation 38 relative to the wild type copies of the genomic locus 34, to produce an amplified sample. The amplifying is done using a first primer 40 and a second primer 42, where the first primer comprises a 3' terminal nucleotide 44 that base pairs with the point mutation and also comprises a nucleotide sequence that is fully complementary to a sequence in the locus with the exception of a single base mismatch 46 (i.e., a base that is not complementary to the corresponding base in the target genomic locus) within 6 bases of 3' terminal nucleotide 44. The presence of product 30 in the amplified sample is detected using a flap assay that employs an invasive oligonucleotide 48 having a 3' terminal nucleotide that base pairs with the point mutation. As shown in FIG. 2, the first primer 40 is employed as the invasive oligonucleotide 48 in the flap assay, although, in alternative embodiments, a second oligonucleotide that is distinct from the first primer may be used. As described above and in FIG. 1, the flap assay relies on the cleavage of complex 32 that contains a flap oligonucleotide 50, invasive oligonucleotide 48 and product 30 by a flap endonuclease (not shown) to release flap 52. Released flap 52 then hybridizes to FRET cassette 54 to form a second complex that is cleaved by the flap endonuclease to cleave the fluorophore from the complex and generate fluorescent signal 56 that can be measured to indicate the amount of product in the amplified sample.

The amount of product in the sample may be normalized relative to the amount of a control nucleic acid present in the sample, thereby determining a relative amount of the mutant copies in the sample. In some embodiments, the control nucleic acid may be a different locus to the genomic locus and, in certain cases, may be detected using a flap assay that employs an invasive oligonucleotide having a 3' terminal nucleotide that base pairs with the wild type copies of the genomic locus at the site of the point mutation, thereby detecting the presence of wild type copies of the genomic locus in said sample. The control may be measured in parallel with measuring the product in the same reaction mixture or a different reaction mix. If the control is measured in the same reaction mixture, the flap assay may include further reagents, particularly a second invasive oligonucleotide, a second flap probe having a second flap and a second FRET cassette that produces a signal that is distinguishable from the FRET cassette used to detect the mutant sequence. In particular embodiments, the reaction mixture may further comprise PCR reagents and flap reagents for amplifying and detecting a second genomic locus or for detecting a second point mutation in the same genomic locus.

In certain cases, fluorescence indicating the amount of cleaved flap can be detected by an automated fluorometer designed to perform real-time PCR having the following features: a light source for exciting the fluorophore of the FRET cassette, a system for heating and cooling reaction mixtures and a fluorometer for measuring fluorescence by the FRET cassette. This combination of features, allows real-time measurement of the cleaved flap, thereby allowing the amount of target nucleic acid in the sample to be quantified. Automated fluorometers for performing real-time PCR reactions are known in the art and can be adapted for use in this specific assay, for example, the ICYCLER™ from Bio-Rad Laboratories (Hercules, Calif.), the Mx3000P™, the MX3005P™ and the MX4000™ from Stratagene (La Jolla, Calif.), the ABI PRISM™ 7300, 7500, 7700, and 7900 Taq Man (Applied Biosystems, Foster City, Calif.), the SMARTCYCLER™, ROTORGENE 2000™ (Corbett Research, Sydney, Australia) and the GENE XPERT™ System (Cepheid, Sunnyvale, Calif.) and the LIGHTCYCLER™ (Roche Diagnostics Corp., Indianapolis, Ind.). The speed of ramping between the different reaction temperatures is not critical and, in certain embodiments, the default ramping speeds that are preset on thermocyclers may be employed.

In certain cases, the method may further involve graphing the amount of cleavage that occurs in several cycles, thereby providing a real time estimate of the abundance of the nucleic acid target. The estimate may be calculated by determining the threshold cycle (i.e., the cycle at which this fluorescence increases above a predetermined threshold; the "Ct" value or "Cp" value). This estimate can be compared to a control (which control may be assayed in the same reaction mix as the genomic locus of interest) to provide a normalized estimate. The thermocycler may also contain a software application for determining the threshold cycle for each of the samples. An exemplary method for determining the threshold cycle is set forth in, e.g., Luu—The et al (Biotechniques 2005 38: 287-293).

A device for performing sample analysis is also provided. In certain embodiments, the device comprises: a) a thermocycler programmed to perform the above-described method and b) a vessel comprising the above-described reaction mixture.

Utility

The method described finds use in a variety of applications, where such applications generally include sample analysis applications in which the presence of a target nucleic acid sequence in a given sample is detected.

In particular, the above-described methods may be employed to diagnose, to predict a response to treatment, or to investigate a cancerous condition or another mammalian disease, including but not limited to, leukemia, breast carcinoma, prostate cancer, Alzheimer's disease, Parkinsons's disease, epilepsy, amylotrophic lateral schlerosis, multiple sclerosis, stroke, autism, mental retardation, and developmental disorders. Many nucleotide polymorphisms are associated with and are thought to be a factor in producing these disorders. Knowing the type and the location of the nucleotide polymorphism may greatly aid the diagnosis, prognosis, and understanding of various mammalian diseases. In addition, the assay conditions described herein can be employed in other nucleic acid detection applications including, for example, for the detection of infectious diseases, viral load monitoring, viral genotyping, environmental testing, food testing, forensics, epidemiology, and other areas where specific nucleic acid sequence detection is of use.

In some embodiments, a biological sample may be obtained from a patient, and the sample may be analyzed using the method. In particular embodiments, the method may be employed to identify and/or estimate the amount of mutant copies of a genomic locus that are in a biological sample that contains both wild type copies of a genomic locus and mutant copies of the genomic locus that have a point mutation relative to the wild type copies of the genomic locus. In this example, the sample may contain at least 100 times (e.g., at least 1,000 times, at least 5,000 times, at least 10,000 times, at least 50,000 times or at least 100,000 times) more wild type copies of the genomic locus than mutant copies said genomic locus.

In these embodiments, the method may be employed to detect an oncogenic mutation (which may be a somatic mutation) in, e.g., PIK3CA, NRAS, KRAS, JAK2, HRAS, FGFR3, FGFR1, EGFR, CDK4, BRAF, RET, PGDFRA, KIT or ERBB2, which mutation may be associated with breast cancer, melanoma, renal cancer, endometrial cancer, ovarian cancer, pancreatic cancer, leukemia, colorectal cancer, prostate cancer, mesothelioma, glioma, medullobastoma, polycythemia, lymphoma, sarcoma or multiple myeloma (see, e.g., Chial 2008 Proto-oncogenes to oncogenes to cancer. Nature Education 1:1).

In these embodiments, the reaction mixture may contain a first primer and a second primer wherein the first primer comprises a 3' terminal nucleotide that base pairs with the point mutation. The first primer may be employed as the invasive oligonucleotide in the second set of cycles or, in certain cases, there may be a separate invasive oligonucleotide present in the reaction mixture that also has a 3' terminal nucleotide that base pairs with the point mutation. Since the point mutation in the genomic locus may have a direct association with cancer, e.g., colorectal cancer, the subject method may be employed to diagnose patients with cancer or a pre-cancerous condition (e.g., adenoma etc.), alone, or in combination with other clinical techniques (e.g., a physical examination, such as, a colonoscopy) or molecular techniques (e.g., immunohistochemical analysis). For example, results obtained from the subject assay may be combined with other information, e.g., information regarding the methylation status of other loci, information regarding rearrangements or substitutions in the same locus or at a different locus, cytogenetic information, information regarding rearrangements, gene expression information or information about the length of telomeres, to provide an overall diagnosis of cancer or other diseases.

In one embodiment, a sample may be collected from a patient at a first location, e.g., in a clinical setting such as in a hospital or at a doctor's office, and the sample may be forwarded to a second location, e.g., a laboratory where it is processed and the above-described method is performed to generate a report. A "report" as described herein, is an electronic or tangible document which includes report elements that provide test results that may include a Ct value, or Cp value, or the like that indicates the presence of mutant copies of the genomic locus in the sample. Once generated, the report may be forwarded to another location (which may the same location as the first location), where it may be interpreted by a health professional (e.g., a clinician, a laboratory technician, or a physician such as an oncologist, surgeon, pathologist), as part of a clinical diagnosis.

Kits

Also provided are kits for practicing the subject method, as described above. The components of the kit may be present in separate containers, or multiple components may be present in a single container. In particular embodiments, a kit may comprise: a) PCR reagents that include a first primer and a second primer, wherein the first primer comprises a 3' terminal nucleotide that base pairs with a point mutation in a genomic locus and also comprises a nucleotide sequence that is fully complementary to a sequence in the genomic locus with the exception of a single base mismatch within 6 bases of the 3' terminal nucleotide; and b) flap assay reagents that include an invasive oligonucleotide having a 3' terminal nucleotide that base pairs with the point mutation. The particulars of these reagents are described above. The kit further comprises PCR and flap reagents for amplification and detection of a control nucleic acid.

In addition to above-mentioned components, the kit may further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to the instructions, the kits may also include one or more control samples, e.g., positive or negative controls analytes for use in testing the kit.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

EXAMPLE 1

KRAS G35A assay

The assay described below is designed to detect nucleic acid sequences containing the KRAS G35A mutation in a background of wild type sequences. For reference, partial nucleotide sequences for the wild type and G35A mutant alleles of KRAS are shown below.

Partial sequence of amplification region for KRAS, wild type (position 35 underlined):

(SEQ ID NO: 1)
CATTATTTTTATTATAAGGCCTGCTGAAAATGACTGAATATAAACTTGT

GGTAGTTGGAGCTGGTGGCGTAGGCAAGAGTGCCTTGACGATACAGCTA

ATTCAGAATCATTTTGTGGACGAATATGATCCAACAATAGA

Partial sequence of amplification region for KRAS, mutant G35A (position 35 underlined):

(SEQ ID NO: 2)
CATTATTTTTATTATAAGGCCTGCTGAAAATGACTGAATATAAACTTGT

GGTAGTTGGAGCTGATGGCGTAGGCAAGAGTGCCTTGACGATACAGCTA

ATTCAGAATCATTTTGTGGACGAATATGATCCAACAATAGA

In this experiment, the entire burden of specificity for detection and discrimination of the G35A mutation rested upon the flap probe. Forward and reverse primer binding regions were outside of the mutation at position 35. The invasive oligonucleotide was not the same sequence as either of the primers. Primers for the amplification of this region were 5'-AGGCCTGCTGAAAATGACTG-3' (SEQ ID NO:3) and 5'-TTGTTGGATCATATTCGTCCAC-3' (SEQ ID NO:4).

The homogeneous detection of the KRAS G35A mutation was accomplished by the use of an endonuclease cleavable flap probe, an invasive oligonucleotide probe, a cleavable FRET cassette, and a heat stable flap endonuclease. For the detection of the G35A mutation, the flap probe sequence was 5'-CGCCGAGGATGGCGTAGGCA-3'/3C6/(SEQ ID NO:5), where the mutant base is shown underlined and the 3'-end is blocked with a hexanediol group in order to inhibit primer extension. The cleaved flap portion, which subsequently binds the FRET cassette, and in turn releases the fluorophore away from its quencher, includes all of the bases from the 5'-end to the mutation-specific A. The invasive oligonucleotide used in this example was 5'-TGTGGTAGTTG-GAGCTGg-3' (SEQ ID NO:6), where the 3' g is not specific for the G35A. Primers, invasive oligos, and flap probes were supplied as non-catalog items by Integrated DNA Technologies (IDT, Coralville, Iowa).

The FRET cassette used was /Red/TCT/Quencher/TCG-GCCTTTTGGCCGAGAGACCTCGG CGCG/3C6/(SEQ ID NO:7), where Redmond Red is the fluorescent dye, the quencher is the Eclipse® Dark Quencher, and the 3'-end is blocked with a hexanediol group in order to inhibit primer extension. The FRET cassette was supplied by Hologic (Madison, Wis.). This FRET cassette may be referred to as Arm 1 Red FRET cassette).

The relative positioning of the primers, invasive probe, and flap probe binding region can be seen as underlined regions on the following sequence, with the flap probe binding region shown italicized:

(SEQ ID NO: 8)
CATTATTTTTATTATA<u>AGGCCTGCTGAAAATGACTGAATATAAACT</u><u>TGT</u>

<u>GGTAGTTGGAGCTGA</u>*<u>TGGCGTAGGC</u>*AAGAGTGCCTTGACGATACAGCTA

ATTCAGAATCATTTT<u>GTGGACGAATATGATCCAACAATAGA</u>

Cycling conditions were 95° C. for 2 min; 50 cycles at 95° C. for 20 sec, 50° C. for 1 min, and 70° C. for 30 sec, with a final 40° C. hold. Fluorescent signal acquisition was done at the 50° C. point in the cycle. The PCR reactions were done in LightCycler® 480 Multiwell 96 Plates (Roche, Indianapolis) in 10 mM MOPS pH 7.5, with 7.5 mM $MgCl_2$, and 250 µM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, invasive oligo probe was at 70 nM, and the FRET cassette was used at a final concentration of 200 nM. All amplification and detection was performed in the LightCycler 480 optical thermocycler (Roche, Indianapolis, Ind.).

Plasmids containing fragments of the KRAS gene, either the wild type or the mutant, were used to assess the ability of the experimental system to detect KRAS 35A mutant copies spiked in wild-type copies at 4 different levels of the mutant, including $10^4$ mutant copies in $10^5$ wild-type copies (1:10), $10^3$ mutant copies in $10^5$ wild-type copies (1:100), $10^2$ mutant copies in $10^5$ wild-type copies (1:1000), and 10 mutant copies in $10^5$ wild-type copies (1:10000).

Figure 3:
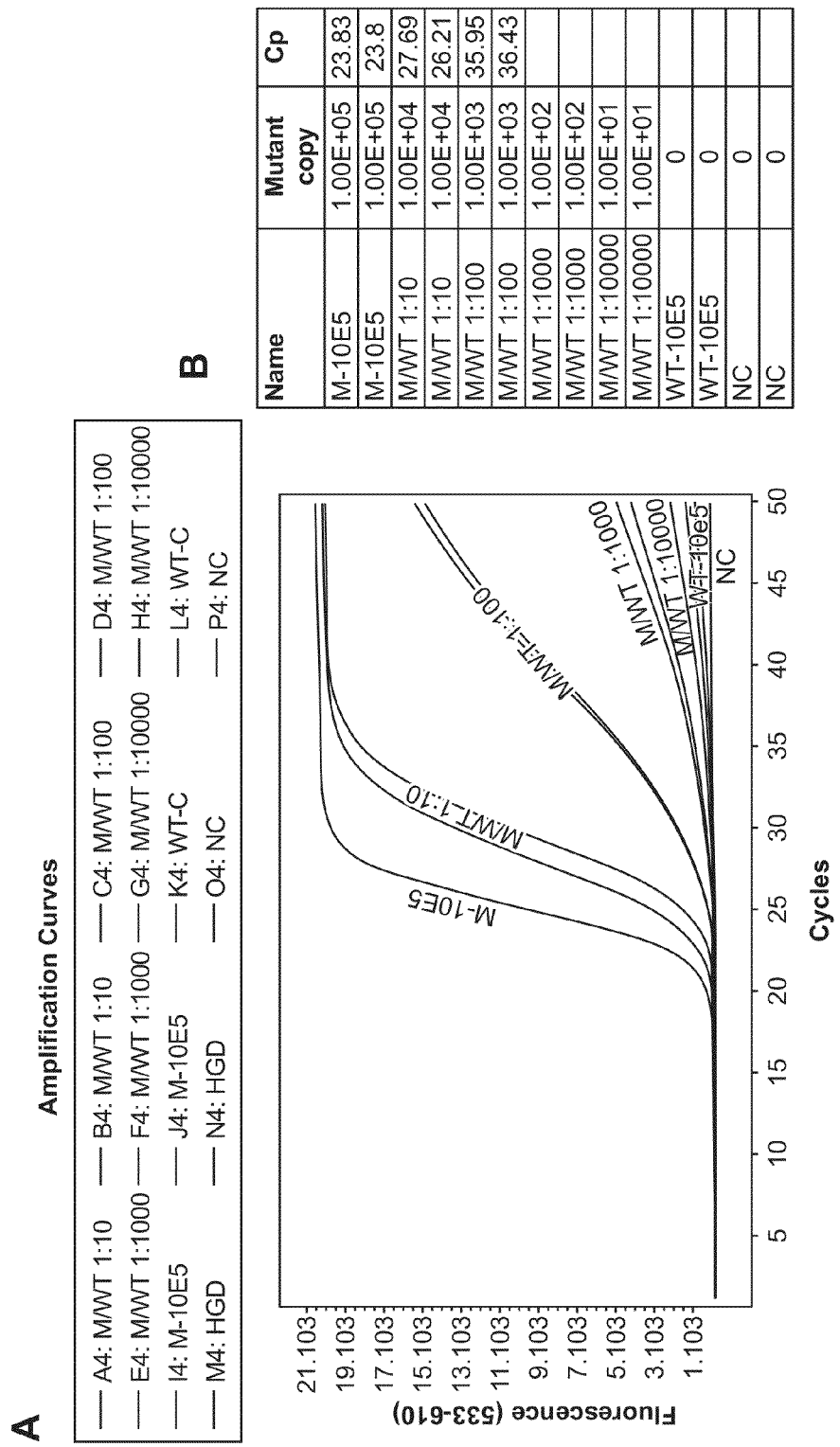
FIG. 3 panels A and B provide data in the form of a graph (panel A) and a table (panel B) that are described in greater detail in the Examples section of this disclosure.

Data showing kinetic amplification curves and the "crossing point" (Cp; Roche LightCycler 480 Manual, Indianapolis, Ind.) of the different ratios of mutant to wild type in the amplification samples are shown in FIG. 3. In these assays, the Cp is calculated as being the point at which fluorescence rose to 18% of the maximum fluorescence. The design of primers, invasive probe, and flap probe used in this example were unable to detect the G35A mutation when there were greater than 100-fold more wild type than mutant forms of the gene.

EXAMPLE 2

KRAS G35A assay

As in Example 1, this assay was designed to detect the G35A mutation in the presence of various levels of the wild type sequence. Mutant and wild type sequence are as described in Example 1 (SEQ ID NO:1 and SEQ ID NO:2). In this assay, the forward primer also served to function as the invasive oligonucleotide. The 3' of the forward primer and the pivotal position in the flap probe both contain the mutant-like A base.

Primers used were 5'-TTGTGGTAGTTGGAGCTGA-3' (SEQ ID NO:9), where the underlined 3' base corresponds to the mutation, and 5'-CTATTGTTGGATCATATTCGTC-3' (SEQ ID NO:10). The flap probe used was the same as in Example 1, 5'-CGCCGAGGATGGCGTAGGCA-3'/3C6/ (SEQ ID NO:5), where the mutant base is shown underlined and the 3'-end is blocked with a hexanediol group in order to inhibit primer extension. Primers and flap probes were supplied as non-catalog items by Integrated DNA Technologies (IDT, Coralville, Iowa).

The relative positioning of the primers, invasive probe, and flap probe binding region can be seen as underlined regions on the following sequence, with the flap probe binding region shown italicized:

(SEQ ID NO: 11)
CATTATTTTTATTATAAGGCCTGCTGAAAATGACTGAATATAAAC<u>TTGT</u>

<u>GGTAGTTGGAGCTGA</u>*TGGCGTAGGC*AAGAGTGCCTTGACGATACAGCTA

ATTCAGAATCATTTTGTG<u>GACGAATATGATCCAACAATAGA</u>

The FRET cassette used was /Red/TCT/Quencher/TCG-GCCTTTTGGCCGAGAGACCTCGGCGCG/3C6/ (SEQ ID NO: 25) where Redmond Red is the fluorescent dye, the quencher is the Eclipse® Dark Quencher, and the 3'-end is blocked with a hexanediol group in order to inhibit primer extension. The FRET cassette was supplied by Hologic (Madison, Wis.).

Cycling conditions were 95° C. for 2 min; 50 cycles at 95° C. for 20 sec, 53° C. for 1 min, and 70° C. for 30 sec; and 40° C. to hold. Fluorescent signal acquisition was done at the 53° C. point in the cycle. The PCR reactions were done in LightCycler® 480 Multiwell 96 Plates (Roche, Indianapolis) in 10 mM MOPS pH 7.5, with 7.5 mM $MgCl_2$, and 250 µM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, and the FRET cassette was used at a final concentration of 200 nM. All amplification and detection was performed in the LightCycler 480 optical thermocycler (Roche, Indianapolis, Ind.).

Plasmids containing fragments of the KRAS gene, either the wild type or the mutant, were used to assess the ability of the experimental system to detect KRAS 35A mutant copies spiked in wild-type copies at 4 different levels of the mutant, including $10^4$ mutant copies in $10^5$ wild-type copies (1:10), $10^3$ mutant copies in $10^5$ wild-type copies (1:100), $10^2$ mutant copies in $10^5$ wild-type copies (1:1000), and 10 mutant copies in $10^5$ wild-type copies (1:10000).

Figure 4:
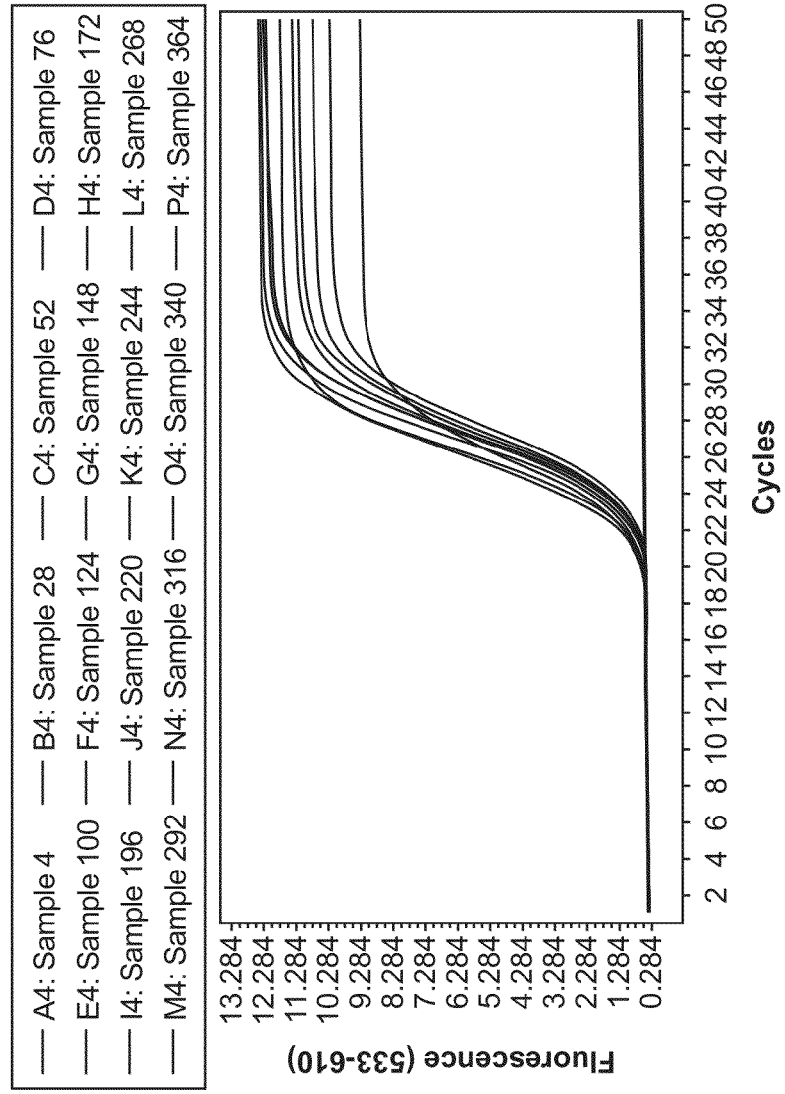
FIG. 4 panels A and B provide data in the form of a graph (panel A) and a table (panel B) that are described in greater detail in the Examples section of this disclosure.

Data showing kinetic amplification curves and the "crossing point" (Cp; Roche LightCycler 480 Manual, Indianapolis, Ind.) of the different ratios of mutant to wild type in the amplification samples are shown in FIG. 4. In these assays, the Cp is calculated as being the point at which fluorescence rose to 18% of the maximum fluorescence. The design of primers and flap probe used in this example were unable to detect the G35A mutation in the presence of wild type, and there is no real dose response.

EXAMPLE 3

KRAS G35A, G35T, and G35C Assays with Secondary Mismatches

In this example, secondary mismatches were added to the forward primer, which also acts as the invasive probe in these cleavage assays. The second mismatch was added to the fourth base, counting from the 3' end base that matches the mutation. In all cases, the second mismatch base was an A, corresponding to a C in the sequence, and thus generating an A:G mispair in the mutant and wild type sequences. The destablizing A mismatch was employed with primers (which are also the invasive probe) that had 3' ends with A, T, or C, corresponding to all of the three mutations found at position 35 of KRAS.

The target sequence for the wild type KRAS is as in Example 1 (SEQ ID NO:1). The G35A sequence detected was the one shown in Example 1 (SEQ ID NO:2).

Partial sequence of amplification region for KRAS, mutant G35T (position 35 underlined):

(SEQ ID NO: 12)
CATTATTTTTATTATAAGGCCTGCTGAAAATGACTGAATATAAACTTGT

GGTAGTTGGAGCTGTTGGCGTAGGCAAGAGTGCCTTGACGATACAGCTA

ATTCAGAATCATTTTGTGGACGAATATGATCCAACAATAGA

Partial sequence of amplification region for KRAS, mutant G35C (position 35 underlined):

(SEQ ID NO: 13)
CATTATTTTTATTATAAGGCCTGCTGAAAATGACTGAATATAAACTTGT

GGTAGTTGGAGCTGCTGGCGTAGGCAAGAGTGCCTTGACGATACAGCTA

ATTCAGAATCATTTTGTGGACGAATATGATCCAACAATAGA

The reverse primer used for all three of these mutation detection designs was the same as the one in Example 2,5'-CTATTGTTGGATCATATTCGTC-3' (SEQ ID NO:10). The forward primer for detection of the G35A was 5'-TTGTGGTAGTTGGAGATGA-3' (SEQ ID NO:14) where the 3' end underlined base corresponds to the mutation targeted and the underlined base four positions from the 3' end is the destablizing mismatch intended to augment the effect of the 3' end mismatch. The flap probe used for G35A was the same as in Example 1,5'-CGCCGAGGATGGCGTAGGCA-3'/3C6/(SEQ ID NO:5), where the mutant base is shown underlined and the 3'-end is blocked with a hexanediol group in order to inhibit primer extension.

The forward primer for detection of the G35T was 5'-TTGTGGTAGTTGGAGATGT-3' (SEQ ID NO:15) where the 3' end underlined base corresponds to the mutation targeted and the underlined base four positions from the 3' end is the destablizing mismatch intended to augment the effect of the 3' end mismatch. The flap probe used for G35T was 5'-CGCCGAGGTTGGCGTAGGCA-3'/3C6/(SEQ ID NO:16), where the mutant base is shown underlined and the 3'-end is blocked with a hexanediol group in order to inhibit primer extension.

The forward primer for detection of the G35C was 5'-TTGTGGTAGTTGGAGATGC-3' (SEQ ID NO:17) where the 3' end underlined base corresponds to the mutation targeted and the underlined base, four positions from the 3' end is the destablizing mismatch intended to augment the effect of the 3' end mismatch. The flap probe used for G35C was 5'-CGCCGAGGCTGGCGTAGGCA-3'/3C6/(SEQ ID NO:18), where the mutant base is shown underlined and the 3'-end is blocked with a hexanediol group in order to inhibit primer extension.

The spatial configuration of primers and flap probe is similar to that shown in Example 2 (SEQ ID NO:11).

Primers and flap probes were supplied as non-catalog items by Integrated DNA Technologies (IDT, Coralville, Iowa).

The FRET cassette used, for all of these mutation detection systems used /Red/TCT/Quencher/TCGGCCTTTTGGC-CGAGAGACCTCGGCGCG/3C6/(SEQ ID NO:30), where Redmond Red is the fluorophore, the quencher is the Eclipse® Dark Quencher, and the 3'-end is blocked with a hexanediol group in order to inhibit primer extension. The FRET cassette was supplied by Hologic (Madison, Wis.).

Cycling conditions were 95° C. for 2 min; 50 cycles at 95° C. for 20 sec, 53° C. for 1 min, and 70° C. for 30 sec; and 40° C. to hold. Fluorescent signal acquisition was done at the 53° C. point in the cycle. The PCR reactions were done in Light-Cycler® 480 Multiwell 96 Plates (Roche, Indianapolis) in 10 mM MOPS pH 7.5, with 7.5 mM $MgCl_2$, and 250 μM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, and the FRET cassette was used at a final concentration of 200 nM. All amplification and detection was performed in the LightCycler 480 optical thermocycler (Roche, Indianapolis, Ind.).

Plasmids containing fragments of the KRAS gene, either the wild type or respectively one of the three mutants, were used to assess the ability of the experimental system to detect KRAS G35A, T, or C mutant copies spiked in wild-type copies at 4 different levels of the mutant, including $10^4$ mutant copies in $10^5$ wild-type copies (1:10), $10^3$ mutant copies in $10^5$ wild-type copies (1:100), $10^2$ mutant copies in $10^5$ wild-type copies (1:1000), and 10 mutant copies in $10^5$ wild-type copies (1:10000).

Figure 5:
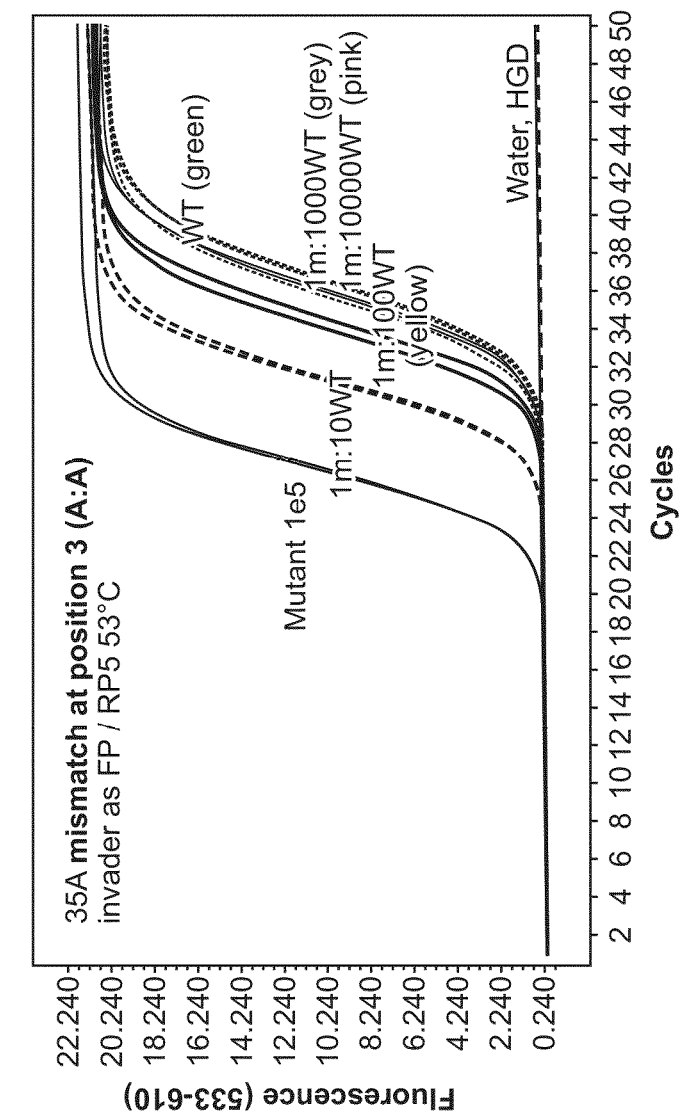
FIG. 5 panels A-F provide data in the form of graphs (panels A, B and C) and table (panels D, E and F) that are described in greater detail in the Examples section of this application.

Data showing kinetic amplification curves and the "crossing point" (Cp; Roche LightCycler 480 Manual, Indianapolis, Ind.) of the different ratios of mutant to wild type in the amplification samples are shown in FIG. 5. In these assays, the Cp is calculated as being the point at which fluorescence rose to 18% of the maximum fluorescence. The design of primers and flap probe used in this example could discriminate mutant sequence from wild-type sequence, and its amplification efficiency was not suppressed by excessive amounts of wild-type sequences down to about 1:100 mutant/wild-type ratio. However, the assay could not reliably detect mutant sequences at a 1:1000 mutant/wild-type ratio (FIG. 5).

EXAMPLE 4

KRAS G35A, G35T, and G35C Assays with Other Secondary Mismatches

In this example, secondary mismatches were tested, similar to Example 3, except mismatches known to be more destablizing to base pairing, specifically A-C and C-C mismatches were tested at the penultimate position, adjacent to the 3'-end mismatch, for G35A and G35T, respectively. The same primer set as used in Example 3 was used for detection of G35C. In addition, a different flap arm of the flap probe was used as well as a correspondingly paired FRET cassette.

Target sequences for the three mutations are the same as those described in Example 1 and Example 3. The reverse primer used for all three of these mutation detection experiments was the same as the one in Example 2,5'-CTATTGT-TGGATCATATTCGTC-3' (SEQ ID NO:10).

The forward primer for detection of G35C are the same as described in Example 3,5'-TTGTGGTAGTTGGAGATGC-3' (SEQ ID NO:17) where the 3' end underlined base corresponds to the mutation targeted and the underlined base, four positions from the 3' end is the destablizing mismatch intended to augment the effect of the 3' end mismatch.

The forward primer for detection of the G35A was 5'-TTGTGGTAGTTGGAGCTAA-3' (SEQ ID NO:19) where the 3' end underlined base corresponds to the mutation targeted and the penultimate underlined base is the destablizing mismatch intended to augment the effect of the 3' end mismatch. The forward primer for detection of the G35T was 5'-TTGTGGTAGTTGGAGCTCT-3' (SEQ ID NO:20) where the 3' end underlined base corresponds to the mutation targeted and the penultimate underlined base is the destablizing mismatch intended to augment the effect of the 3' end mismatch.

The flap probe for detection of G35A was 5'-GACGCG-GAGATGGCGTAGGCA-3'/3C6/(SEQ ID NO:21) where the mutant base is shown underlined and the 3'-end is blocked with a hexanediol group in order to inhibit primer extension. The flap probe for detection of G35T was 5'-GACGCGGAG TTGGCGTAGGCA-3'/3C6/(SEQ ID NO:22) where the mutant base is shown underlined and the 3'-end is blocked with a hexanediol group in order to inhibit primer extension. The flap probe for detection of G35C was 5'-GACGCGGAG CTGGCGTAGGCA-3'/3C6/(SEQ ID NO:23) where the mutant base is shown underlined and the 3'-end is blocked with a hexanediol group in order to inhibit primer extension.

The FRET cassette used, for the mutation detection in this example was 5'-FAM/TCT/Quencher/AGCCGGTTTTCCG-GCTGAGACTCCGCGTCCGT-3'/3C6 (SEQ ID NO:24), where FAM is fluorescein, the quencher is the Eclipse® Dark Quencher, and the 3'-end is blocked with a hexanediol group in order to inhibit primer extension. The FRET cassette was supplied by Hologic (Madison, Wis.). Cycling conditions were 95° C. for 2 min; 50 cycles at 95° C. for 20 sec, 53° C. for 1 min, and 70° C. for 30 sec; and 40° C. to hold. Fluorescent signal acquisition was done at the 53° C. point in the cycle. The PCR reactions were done in LightCycler® 480 Multiwell 96 Plates (Roche, Indianapolis) in 10 mM MOPS pH 7.5, with 7.5 mM MgCl$_2$, and 250 µM dNTPs (Promega, Madison, Wis.). Taq polymerase was the iTaq enzyme (Bio-Rad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, and the FRET cassette was used at a final concentration of 200 nM. All amplification and detection was performed in the LightCycler 480 optical thermocycler (Roche, Indianapolis, Ind.).

Plasmids containing fragments of the KRAS gene, either the wild type or receptively one of the three mutants, were used to assess the ability of the experimental system to detect KRAS G35A, T, or C mutant copies spiked in wild-type copies at 4 different levels of the mutant, including $10^4$ mutant copies in $10^5$ wild-type copies (1:10), $10^3$ mutant copies in $10^5$ wild-type copies (1:100), $10^2$ mutant copies in $10^5$ wild-type copies (1:1000), and 10 mutant copies in $10^5$ wild-type copies (1:10000).

Figure 6:
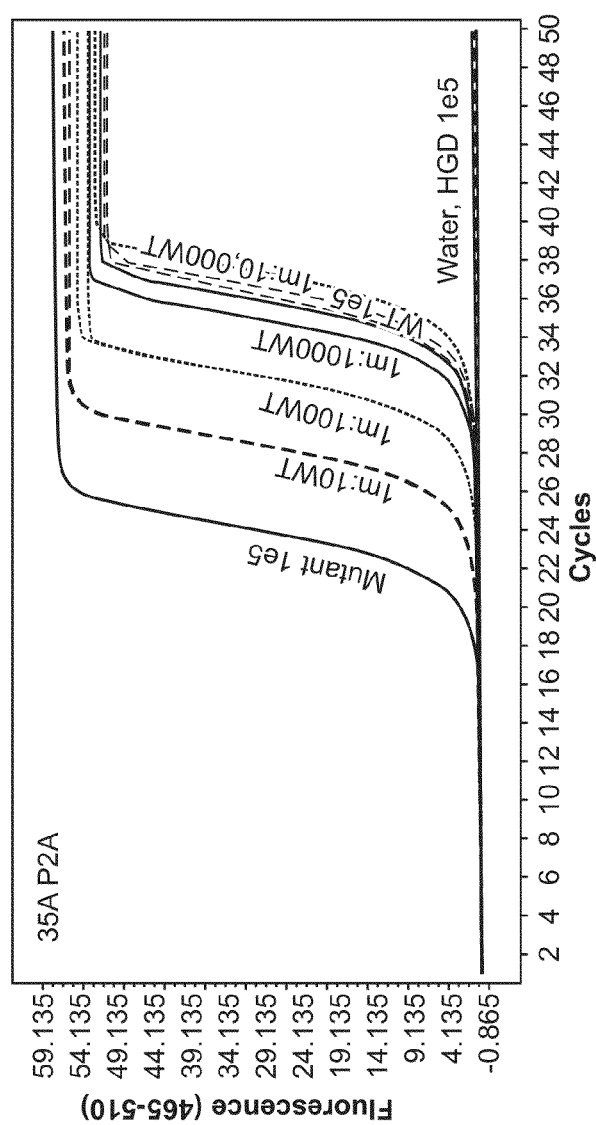
FIG. 6 panels A-F provide data in the form of graphs (panels A, B and C) and table (panels D, E and F) that are described in greater detail in the Examples section of this application.

Data showing kinetic amplification curves and the "crossing point" (Cp; Roche LightCycler 480 Manual, Indianapolis, Ind.) of the different ratios of mutant to wild type in the amplification samples are shown in FIG. 6. In these assays, the Cp is calculated as being the point at which fluorescence rose to 18% of the maximum fluorescence. The design of primers and flap probe used in this example could discriminate mutant sequence from wild-type sequence, and its amplification efficiency was not suppressed by excessive amounts of wild-type sequences. KRAS G35A and G35C assays could linearly detect mutant sequence down to a ratio of 1:1000 mutant/wild-type ratio, and the G35T assay could linearly detect down to a ratio of 1:100 mutant/wild-type ratio (FIG. 6).

EXAMPLE 5

Additional Experimental Determination of Best Secondary Mismatches for KRAS G35A Detection In this example, similar to the previous examples, the destablizing effect of secondary mismatches in the forward primer, which also functions as the invasive probe was tested using the mutation at position 35 of KRAS. As in the other examples, the detection of the G35A mutation was assessed at various ratios compared to an excess of the wild type sequence. Target amplification region sequences were the same as in Example 1 (SEQ ID NO:1 and SEQ ID NO:2). The reverse primer used for all three of these mutation detection experiments was the same as the one in Examples 2, 3, and 4: 5'-CTATTGTTGGATCATATTCGTC-3' (SEQ ID NO:10).

The flap probe (SEQ ID NO:21) and FRET cassette (SEQ ID NO:24) were the same as those used for detection of G35A in Example 4. The series of forward probes, which also serve as invasive oligos for the cleavage assay are listed, where the 3' end underlined base corresponds to the mutation targeted and the other underlined base is the destablizing mismatch intended to augment the effect of the 3' end mismatch.

```
                                              (SEQ ID NO: 25)
KRAS 35A P2C: 5'-TTGTGGTAGTTGGAGCTCA-3'

(SEQ ID NO: 26)
KRAS 35A P4A: 5'-AACTTGTGGTAGTTGGAGATGA-3'

(SEQ ID NO: 27)
KRAS 35A P6T: 5'-CTTGTGGTAGTTGGTGCTGA-3'

(SEQ ID NO: 28)
KRAS 35A P5C: 5'-AACTTGTGGTAGTTGGACCTGA-3'

(SEQ ID NO: 29)
KRAS 35A P3A: 5'-CTTGTGGTAGTTGGAGCAGA-3'
```

Cycling conditions were 95° C. for 2 min; 50 cycles at 95° C. for 20 sec, 53° C. for 1 min, and 70° C. for 30 sec; and 40° C. to hold. Fluorescent signal acquisition was done at the 50° C. point in the cycle. The PCR reactions were done in LightCycler® 480 Multiwell 96 Plates (Roche, Indianapolis) in 10 mM MOPS pH 7.5, with 7.5 mM MgCl$_2$, and 250 µM dNTPs (Promega, Madison, Wis.). Taq polymerase was the iTaq enzyme (BioRad, Hercules, Calif.) and the cleavage enzyme was Cleavase 2.0 (Hologic, Madison, Wis.). Forward primer concentration was 500 nM, reverse primer concentration was 500 nM, flap probe was at 500 nM, and the FRET cassette was used at a final concentration of 200 nM. All amplification and detection was performed in the LightCycler 480 optical thermocycler (Roche, Indianapolis, Ind.).

Plasmids containing fragments of the KRAS gene, either the wild type or respectively one of the three mutants, were used to assess the ability of the experimental system to detect KRAS G35A, T, or C mutant copies spiked in wild-type copies at 4 different levels of the mutant, including $10^4$ mutant copies in $10^5$ wild-type copies (1:10), $10^3$ mutant copies in $10^5$ wild-type copies (1:100), $10^2$ mutant copies in $10^5$ wild-type copies (1:1000), and 10 mutant copies in $10^5$ wild-type copies (1:10000).

Figure 7:
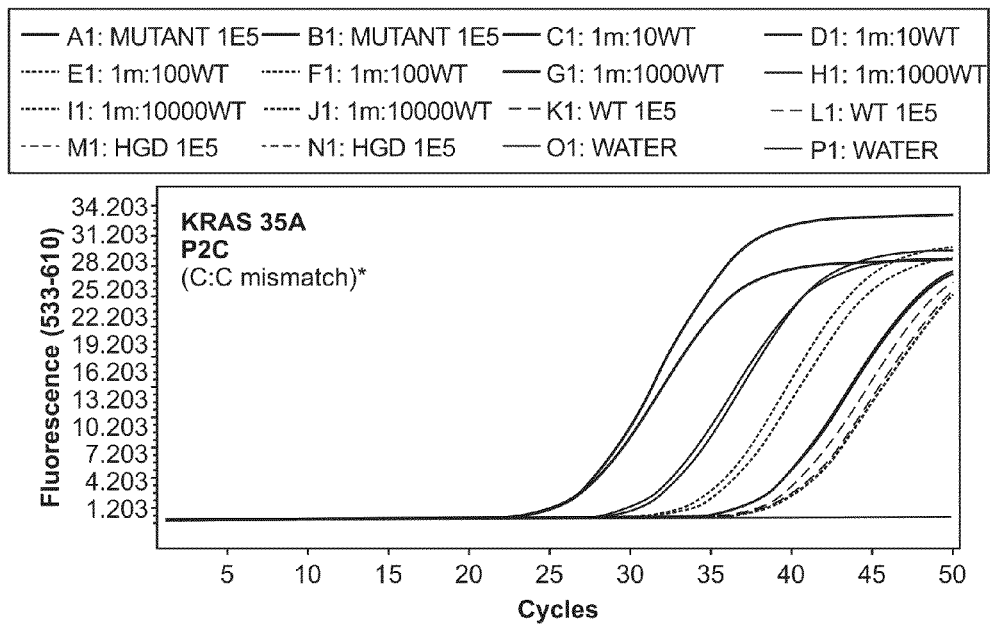
FIG. 7 panels A-F provide data in the form of graphs (panels A-E) and table (panel F) that are described in greater detail in the Examples section of this application.
Figure 7:
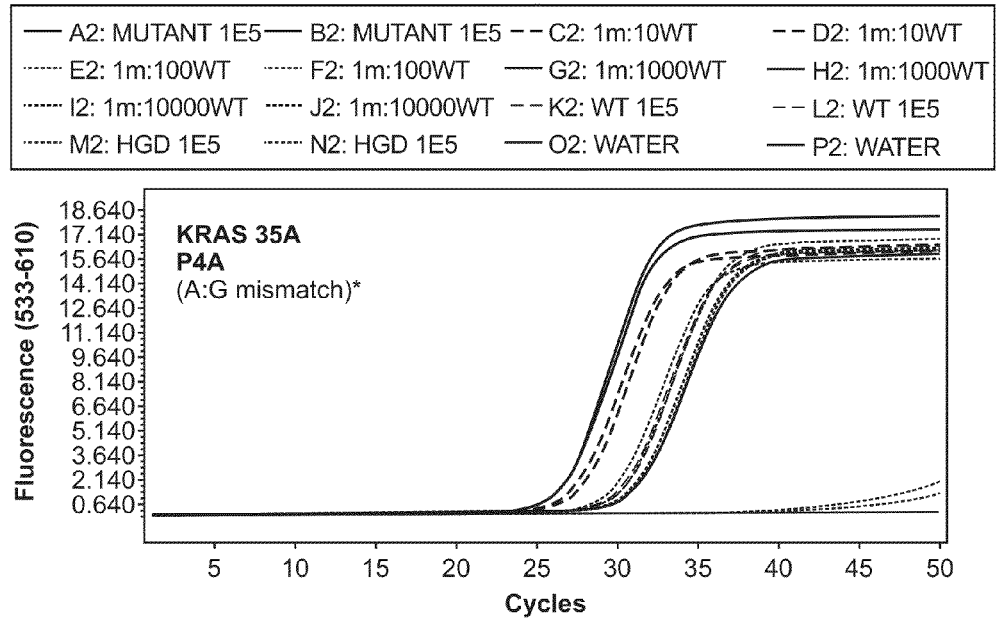

Data showing kinetic amplification curves and the "crossing point" (Cp; Roche LightCycler 480 Manual, Indianapolis, Ind.)" of the different ratios of mutant to wild type in the amplification samples are shown in FIG. 7. In these assays, the Cp is calculated as being the point at which fluorescence rose to 18% of the maximum fluorescence. Out of the 5 primer/invasive probe designs tested, the penultimate mismatch, yielding a C:C mispair, designated KRAS 35A P2C showed the best ability to quantify mutant in the presence of excess wild type gene sequence, showing a dose response to a level of 1:1000 mutant/wild type (FIG. 7).

What is claimed is:

1. A method of sample analysis comprising:
   a) amplifying a product from a sample that comprises both wild type copies of a genomic locus and mutant copies of said genomic locus that have a point mutation relative to said wild type copies of the genomic locus, to produce an amplified sample;
   wherein:
   i. said amplifying is done using a first primer and a second primer; and
   ii. said first primer comprises a 3' terminal nucleotide that base pairs with said point mutation and also comprises a nucleotide sequence that is fully complementary to a sequence in said locus with the exception of a single base mismatch within 6 bases of said 3' terminal nucleotide;
   b) detecting the presence of said product in said amplified sample using a flap assay that employs:
   i. said first primer; and
   ii. a flap oligonucleotide that comprises a nucleotide that base pairs with said point mutation.

2. The method of claim 1, wherein said sample contains at least 100 times more wild type copies of said genomic locus than mutant copies of said genomic locus.

3. The method of claim 1, further comprising normalizing the amount of said product in said amplified sample relative to the amount of a control nucleic acid present in said sample, thereby determining the amount of said mutant copies in said sample.

4. The method of claim 3, wherein said control nucleic acid is a locus different from said genomic locus.

5. The method of claim 3, wherein said control nucleic acid is detected using a flap assay that employs an invasive oligonucleotide having a 3' terminal nucleotide that base pairs with said wild type copies of said genomic locus at the site of said point mutation, thereby detecting the presence of wild type copies of said genomic locus in said sample.

6. The method of claim 3, wherein the said flap assay employs first flap assay reagents that include said first PCR primer, a first flap probe having a first flap and a first FRET cassette, and wherein said control nucleic acid is detected using second flap assay regents that include a second PCR primer, a second flap probe having a second flap and a second FRET cassette that produces a signal that is distinguishable from the first FRET cassette, wherein the first and second flap reagents are in same reaction mixture.

7. The method of claim 1, wherein mutation of said genomic locus is associated with cancer.

8. The method of claim 7, wherein said genomic locus is the KRAS gene.

9. The method of claim 7, wherein said genomic locus is the BRAF gene.

10. The method of claim 1, wherein said sample is obtained from a human.

11. The method of claim 10, wherein sample is stool.

12. The method of claim 11, further comprising making a diagnosis of colon cancer or adenoma based on whether mutant copies of said genomic locus are identified in said stool.

13. The method of claim 1, wherein said mismatch in said first primer is at position −1, position −2, position −3, position −4 or position −5 relative to said terminal nucleotide.

14. The method of claim 1, wherein said amplifying and detecting steps are done using a reaction mixture that contains both PCR reagents and flap reagents, and no additional reagents are added to said reaction mixture between said amplifying and detecting steps.

15. The method of claim 14, wherein said reaction mixture further comprises PCR reagents and flap reagents for amplifying and detecting a second genomic locus.

16. The method of claim 14, wherein said reaction mixture further comprises PCR reagents and flap reagents for amplifying and detecting a point mutation in said second genomic locus.

17. A reaction mixture comprising:
a) amplification reagents comprising a thermostable polymerase, nucleotides, a first primer and a second primer for amplifying a target genomic locus from a nucleic acid sample; wherein said first primer:
  i. comprises a 3' terminal nucleotide that base pairs with a point mutation in said genomic locus; and
  ii. comprises a nucleotide sequence that is fully complementary to a sequence in said locus with the exception of a single base mismatch within 6 bases of said 3' terminal nucleotide;
b) flap assay reagents comprising a flap endonuclease, a FRET cassette and a flap oligonucleotide that comprises a nucleotide that base pairs with said point mutation;
c) said nucleic acid sample, wherein said nucleic acid sample comprises both wild type copies of said genomic locus and mutant copies of said genomic locus that have a point mutation relative to said wild type copies of the genomic locus;
wherein the reaction mixture does not comprise an invasive oligonucleotide distinct from said first primer and wherein said reaction mixture is characterized in that it can amplify and detect the presence of said mutant copies of said genomic locus in said sample.

* * * * *